US007432063B2

(12) United States Patent
Balint et al.

(10) Patent No.: US 7,432,063 B2
(45) Date of Patent: *Oct. 7, 2008

(54) METHODS FOR AFFINITY MATURATION

(75) Inventors: Robert F. Balint, Palo Alto, CA (US); Jeng-Horng Her, San Jose, CA (US)

(73) Assignee: KaloBios Pharmaceuticals, Inc., Palo Alto, CA (US)

( * ) Notice: Subject to any disclaimer, the term of this patent is extended or adjusted under 35 U.S.C. 154(b) by 122 days.

This patent is subject to a terminal disclaimer.

(21) Appl. No.: 10/677,131

(22) Filed: Sep. 30, 2003

(65) Prior Publication Data

US 2004/0132066 A1 Jul. 8, 2004

Related U.S. Application Data

(63) Continuation-in-part of application No. 10/076,845, filed on Feb. 14, 2002, and a continuation-in-part of application No. 10/208,730, filed on Jul. 29, 2002.

(60) Provisional application No. 60/447,846, filed on Feb. 13, 2003, provisional application No. 60/379,718, filed on May 10, 2002, provisional application No. 60/373,802, filed on Apr. 18, 2002, provisional application No. 60/373,765, filed on Apr. 18, 2002.

(51) Int. Cl.
*G01N 33/53* (2006.01)
*C07H 21/04* (2006.01)

(52) U.S. Cl. ............................... 435/7.1; 435/6; 435/4

(58) Field of Classification Search ................ 435/7.1, 435/6, 4
See application file for complete search history.

(56) References Cited

U.S. PATENT DOCUMENTS

| 5,503,977 | A | | 4/1996 | Johnsson et al. |
| 5,925,523 | A | * | 7/1999 | Dove et al. ........................ 435/6 |
| 6,057,101 | A | * | 5/2000 | Nandabalan et al. ............ 435/6 |
| 6,270,964 | B1 | | 8/2001 | Michnick et al. |
| 6,294,330 | B1 | | 9/2001 | Michnick et al. |
| 6,342,345 | B1 | | 1/2002 | Blau et al. |
| 6,974,684 | B2 | * | 12/2005 | Anderson et al. ........... 435/69.1 |
| 2002/0155502 | A1 | | 10/2002 | Balint et al. |
| 2003/0054413 | A1 | | 3/2003 | Kumaraswamy et al. |
| 2003/0157579 | A1 | | 8/2003 | Balint et al. |
| 2003/0175838 | A1 | | 9/2003 | Blau et al. |
| 2005/0008625 | A1 | | 1/2005 | Balint et al. |
| 2005/0142623 | A1 | * | 6/2005 | Yanagawa et al. ........... 435/7.92 |

FOREIGN PATENT DOCUMENTS

| WO | WO 98/44350 A1 | 10/1998 |
| WO | WO 00/71702 A1 | 11/2000 |
| WO | WO 01/51629 A2 | 7/2001 |

OTHER PUBLICATIONS

Wigley et al, Nature Biotechnology, 19, 2001, 131-136.*
Chen, L., et al., "Highly sensitive biological and chemical sensors based on reversible fluorescence quenching in a conjugated polymer," *PNAS*, Oct. 26, 1999, vol. 96, No. 22, 12287-12292.
Johnsson, N. et al., "Split ubiquitin as a sensor of protein interactions in vivo," *Proc. Natl. Acad. Sci. USA*, Oct. 1994, vol. 91, pp. 10340-10344.
Petrosino, Joseph et al.; "Contributions of aspartate 49 and phenylalanine 142 residues of a tight binding Inhibitory protein of β-lactamases"; *The Journal of Biological Chemistry*; Jan. 22, 1999; pp. 2394-2400; vol. 274, No. 4; The American Society for Biochemistry and Molecular Biology, Inc.; USA.
Rossi, F., et al., "Monitoring protein-protein interactions in intact eukaryotic cells by β-galactosidase complementation," *Proc. Natl. Acad. Sci. USA*, Aug. 1997, vol. 94, pp. 3405-3410.
Strynadka, Natalie C. J. et al.; "Structural and kinetic characterization of a β-lactamase-inhibitor protein"; *Nature*; Apr. 14, 1994; pp. 657-660; vol. 368.
Wehrman, Tom, et al.; "Protein-protein interactions monitored in mammalian cells via complementation of β-lactamase enzyme fragments;" *PNAS*; Mar. 19, 2002; pp. 3469-3474; 99:6.

* cited by examiner

*Primary Examiner*—T. D. Wessendorf
(74) *Attorney, Agent, or Firm*—Townsend and Townsend and Crew LLP

(57) ABSTRACT

This invention provides methods of obtaining a binding molecule, e.g., an antibody, that has enhanced affinity for a binding partner relative to a reference binding molecule.

26 Claims, 5 Drawing Sheets

METHODS FOR AFFINITY MATURATION

CROSS REFERENCE TO RELATED APPLICATIONS

This application claims benefit of U.S. provisional application No. 60/447,846, filed Feb. 13, 2003; and is a continuation-in-part (CIP) of U.S. application Ser. No. 10/076,845, filed Feb. 14, 2002; and a continuation-in-part (CIP) of U.S. application Ser. No. 10/208,730, filed Jul. 29, 2002, which application claims benefit of priority of U.S. provisional application Nos. 60/373,765, filed Apr. 18, 2002; 60/373,802, filed Apr. 18, 2002; and 60/379,718, filed May 10, 2002. Each application is incorporated by reference herein.

BACKGROUND OF THE INVENTION

This invention provides new methods of selecting a binding protein with enhanced binding affinity for a binding partner relative to a reference binding protein. In particular, the invention provides methods of selecting antibodies with enhanced affinity for an antigen relative to a reference antibody. This process, "affinity maturation", thereby provides binding proteins, e.g., antibodies, with superior binding capabilities.

Antigen-specific antibodies can be produced by a variety of methods including hybridoma technology (e.g., Kohler & Milstein, *Nature* 256:495-497, 1975) or selection in vitro using phage or yeast display libraries (e.g., Hoogenboom et al., *Immunotechnology* 4: 1-20, 1998; Boder & Wittrup, *Methods Enzymol* 328:430-44, 2000). However, antibodies derived from these methods often have sub-optimal binding affinities. Affinity discrimination among nonspecific antibodies in vitro may be accomplished by equilibrating a mutagenic library of the antibody in question with soluble cognate antigen under conditions in which the concentrations of both antibody and antigen are maintained below the target equilibrium dissociation constant. Competition must be avoided to prevent abundant low-affinity variants from excluding rarer high-affinity variants. Operationally, there are two additional requirements: (1) the antibody library must be displayed by a vehicle such as a bacteriophage or a cell, which couples the antibody to its coding sequence, and (2) the antigen must be coupled to a tag which allows quantitative separation of antigen-bound antibody from unbound antibody. The main drawback of these procedures is that for most applications, affinities in the nanomolar $K_d$ range are desired and these antibodies are sufficiently rare to be easily lost at sub-nanomolar working concentrations. Such difficulties have led to selecting for lower dissociation rate constants ($k_d$, off-rates) to improve antibody affinities. Selection for lower off-rates is usually performed under saturating conditions where antigen-antibody complexes remaining intact after a time proportional to the inverse of the target off-rate can be recovered separately from dissociated antibodies. However, in these procedures it is frequently desired that off-rates for antibodies are in the range of $1 \times 10^{-4}$ sec$^{-1}$, which corresponds to a half-life of ~2 hours. Many antibodies and especially antigens undergo significant irreversible denaturation in vitro on such time scales at ambient or physiological temperatures. Also, off-rate selection in the absence of on-rate selection (lower $k_a$) tends to bias the selection toward variants that refold into stable complexes and therefore tend to disfavor increased on-rates.

Thus, there is a need to develop new methods for obtaining binding molecules, e.g, antibodies, that have improved binding affinities for their binding partners. The current invention fulfills this need. Further, for many antibody applications, a successful protocol for affinity maturation in vitro will be one that produces improvements in both on-rate and off-rate while maintaining or increasing the specificity for the intended antigen. The methods described herein also provide these improvements.

BRIEF SUMMARY OF THE INVENTION

The invention provides methods and systems for the identification of test binding ensemble members, e.g., antibodies and antigens, that have a higher affinity for a binding partner than a reference binding molecule. In one embodiment, the invention provides a method that employs a competitive activation system that uses binding affinity as a selective criterion. In another embodiment, the invention provides a method using an auto-inhibited reactivation system. These systems for identifying higher affinity variants may be used with any reporter system that confers a selectable phenotype on the cells, such as color, or the ability to grow under restrictive conditions, and whose activation or inhibition can be made to depend on the interaction of two binding pair members.

In one aspect, the invention provides an in vivo method of affinity maturation by competitive activation to obtain an antibody that has an enhanced affinity for a target antigen relative to that of a reference antibody. In one embodiment, the method comprises:

(a) recombinantly altering a population of host cells by
   (i) introducing into the host cells a library of genes encoding candidate antibodies;
   (ii) introducing into the host cells a competitive activation system comprising a nucleic acid encoding a responder molecule linked to the target antigen, and a nucleic acid encoding a competitor binding molecule linked to an inhibitor of the responder complex;
(b) incubating the host cells under conditions in which the library and competitive activation system are expressed and where the responder molecule is activated when a candidate antibody binds to the target antigen; and
(c) detecting cells having a signal from the responder molecule that corresponds to a candidate antibody binding affinity for the target antigen that is greater than that of the reference antibody, thereby identifying a candidate antibody with an enhanced affinity for the target antigen.

In another embodiment of affinity maturation by competitive activation, the method comprises:

(a) recombinantly altering a population of host cells by
   (i) introducing into the host cells a library of genes encoding candidate antibodies;
   (ii) introducing into the host cells a competitive activation system comprising a nucleic acid encoding a responder molecule linked to the competitor binding molecule, and a nucleic acid encoding an inhibitor linked to the target antigen;
(b) incubating the host cells under conditions in which the library and competitive activation system are expressed and where the responder molecule is activated when a candidate antibody binds to the target antigen; and
(c) detecting cells having a signal from the responder molecule that corresponds to a candidate antibody binding affinity for the target antigen that is greater than that of the reference antibody, thereby identifying a candidate antibody with an enhanced affinity for the target antigen.

In another aspect, the invention provides in vivo methods of affinity maturation using systems based on the reactivation of auto-inhibited responders.

In one embodiment the method comprises:
(a) recombinantly altering a population of host cells by
 (i) introducing into the host cells a competitor that binds to a target antigen with the same specificity as a reference antibody;
 (ii) introducing into the host cells a nucleic acid encoding a reactivator complex comprising a reactivator molecule linked to the target antigen;
 (iii) introducing into the host cells a library of genes, each of which encodes an auto-inhibited responder complex comprising a responder molecule linked to an inhibitor and linked to a candidate antibody;
(b) incubating the host cells under conditions in which the competitor, the reactivator complex, and the auto-inhibited responder library are expressed where the responder molecule is activated when a candidate antibody binds to the target antigen; and
(c) detecting cells having a signal from the responder molecule that corresponds to a candidate antibody binding affinity for the target antigen that is greater than that of the reference antibody, thereby identifying a candidate antibody with an enhanced affinity for the target antigen.

In another embodiment of affinity maturation using a system based on reactivation of an auto-inhibited responder, the method comprises:
(a) recombinantly altering a population of host cells by
 (i) introducing into the host cells a reference binding molecule that binds to a target antigen with the same specificity as a reference antibody
 (ii) introducing into the host cells a nucleic acid encoding an auto-inhibited responder complex comprising a responder molecule linked to an inhibitor and to the target antigen
 (iii) introducing into the host cells a library of genes, each encoding a reactivator complex, wherein each gene encodes a reactivator molecule linked to a candidate antibody;
(b) incubating the host cells under conditions in which the competitor, the auto-inhibited responder-antigen complex, and the reactivator library complex are expressed and where the responder molecule is activated when a candidate antibody binds to the target antigen; and
(c) detecting cells having a signal from the responder molecule that corresponds to a candidate antibody binding affinity for the target antigen that is greater than that of the reference antibody, thereby identifying a candidate antibody with an enhanced affinity for the target antigen.

Any number of responder molecules may be used in affinity maturation methods. Often, the responder molecule is an enzyme.

The competitor binding molecule may be the reference antibody. Such a reference antibody may be an Fab fragment or a single chain Fv. Similarly, the candidate antibodies may be single chain Fvs, Fab fragments, or single V-region domains. Candidate binding molecules include non-antibody binding molecule, e.g., scaffolded peptides or mugatenized natural ligands.

In some embodiments, the library of candidate antibodies comprises hybrid antibodies that have at least one CDR in a $V_H$ or $V_L$ that is different from the reference antibody and is from a natural antibody repertoire. For example, the hybrid antibodies may have either a $V_H$ or $V_L$ from the reference antibody and the corresponding $V_H$ or $V_L$ from a natural antibody repertoire.

In additional embodiments of the invention, the competitor binding molecule may be a nonhuman antibody and the candidate antibodies comprise antibodies with at least one human variable region. The competitor binding molecule may also be a natural ligand of the target antigen that competes with the reference antibody for binding to the target antigen. The competitor binding molecule may also be an artificial non-antibody ligand of the target antigen that competes with the reference antibody for binding to the target antigen.

DETAILED DESCRIPTION OF THE INVENTION

Definitions

Figure 1:
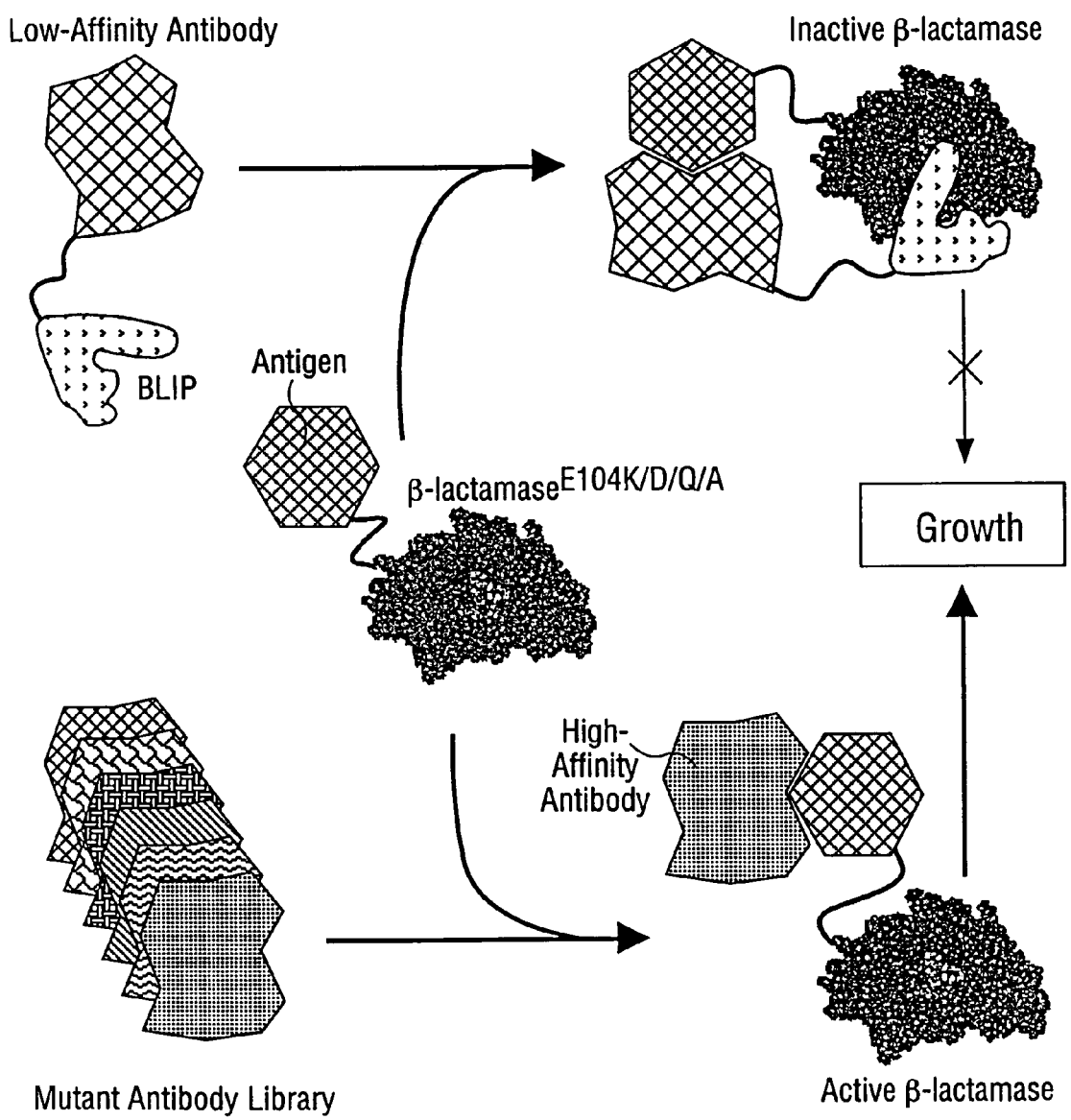
FIG. 1. Affinity maturation of an antibody by COMPACT based on competitive activation of interaction-inhibited β-lactamase. The subject "low-affinity" antibody is genetically fused to either the carboxy-terminus or the amino-terminus of the -β Inhibitor Protein (BLIP) of *Streptomyces clavuligerus* (Strynadka et al., *Nature* 368: 657-660 (1994)) via $(Gly_4Ser)_{3-6}$ linkers. The antigen is similarly fused to either terminus of a variant of TEM-1 β-lactamase, such as the E104K mutant, which has a $K_d$ for BLIP of 10-100M. When these fusions are expressed in the *E. coli* periplasmic space at concentrations which are at least 10-fold higher than the $K_d$ of the antigen-antibody interaction, then the enzyme will be fully inactivated. If an additional gene encoding the same antibody unfused is expressed from a separate plasmid in the same cells at a level which is at least 10-fold lower than that of the fused antibody, it should cause no more than a ~10% activation of the enzyme. Under these conditions any variant of the unfused antibody which has a higher affinity than the parent antibody will produce a greater activation of the enzyme, and will thereby confer on the cells a higher plating efficiency on restrictive concentrations of antibiotic. Successive rounds of replating will allow such variants to be enriched to the point that they can be cleanly separated from the parent and variants which do not have higher affinities. The same system may be used to select for other antibody properties, or for antibodies which compete with other interactions. For example, a mouse antibody which binds a desired epitope on an antigen may be used in the system to guide the selection from human antibody libraries of human antibodies which bind to the same epitope. Alternatively, a target receptor-ligand interaction could be used in the system to guide the selection of human antibodies which specifically interfere with ligand binding, and some of such antibodies may even mimic the signal transducing effects of ligand binding.

The term "affinity matured" in the context of antibodies refers to an antibody that is derived from a reference antibody, e.g., by mutation, binds to the same antigen as the reference antibody; and has a higher affinity for the antigen than that of the reference antibody. Typically, the affinity matured antibody binds to the same epitope as the initial reference antibody. Similarly, an "affinity matured" binding molecule refers to a binding molecule that has a higher affinity for a binding partner relative to a reference binding molecule.

An "affinity maturation system" of the invention refers to a system identifying binding molecules with improved affinity relative to a starting binding molecule. Although other affinity maturation systems exist, in the current invention, these systems are of two types, reactivation or competitive activation systems. A "reactivation system", typically referred to herein as a system of reactivation of auto inhibited responders (RAIR), is a system for detecting binding interactions. Such systems are described, e.g., in co-pending U.S. patent application Ser. No. 10/208,730, filed Jul. 29, 2002. The system involves two complexes, one containing a responder, an inhibitor and a binding ensemble member (the responder complex) and the other comprising a reactivator and a binding ensemble member (the reactivator complex). The responder is inhibited via the action of the inhibitor in its complex. A binding interaction, either direct or indirect, between the binding ensemble members in the responder complex and reactivator complex brings the reactivator into proximity such that the reactivator displaces the inhibitor. The components of the responder complex can be linked to one another in various configurations by covalent or non-covalent linkages.

"Auto-inhibited responder" as used herein refers to a responder which is covalently linked to an inhibitor of the responder, such that the responder is constitutively inhibited unless brought into proximity to a reactivator.

A "reactivator" as used herein refers to a molecule, typically a protein, that can displace an inhibitor from an auto-inhibited responder and thereby activate the responder. In one embodiment, the reactivator binds to the inhibitor. In an alternative embodiment, the reactivator binds to the responder. In another embodiment, the reactivator binds anywhere on the responder complex, e.g., at a junction between two components of the responder complex or to two components of the complex. In preferred embodiments, the binding of reactivator occurs only when it is brought into proximity with the inhibited responder by interaction of the binding ensemble members of the reactivator and responder complexes.

A "competitive activation system" or "COMPACT™ system" as used herein, refers to a system for detecting binding interactions in which a responder molecule is linked, either directly or indirectly to one binding ensemble member; and an inhibitor of the responder molecule is linked, directly or indirectly, to another binding ensemble member. Interaction of the binding ensemble members results in inhibition of responder activity. Such a system may further employ a "mask". These systems are described, e.g., in co-pending U.S. application Ser. No. 10/076,845, filed Feb. 14, 2002.

A "mask", in the context of a competitive activation system, refers to a molecule that has low affinity for a reporter or inhibitor, such that the mask does not bind appreciably at working concentrations unless it is tethered covalently to the reporter or inhibitor. Further, binding of the mask to the inhibitor prevents the inhibitor from binding to the reporter and vice versa. A "mask" inhibits binding of the inhibitor, but does not inhibit reporter activity. A mask allows a high-affinity inhibitor to be used without fear of increasing the background inhibition because its association rate constant is greatly reduced without affecting the dissociation rate constant of the reporter-inhibitor complex, thereby reducing the overall affinity while retaining the stability of the high-affinity reporter-inhibitor complex.

As used herein, an "antibody" refers to a protein functionally defined as a binding protein and structurally defined as comprising an amino acid sequence that is recognized by one of skill as being derived from the framework region of an immunoglobulin encoding gene of an animal producing antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist as intact immunoglobulins or as a number of well characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into an Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Typical antibodies include single chain antibodies (antibodies that exist as a single polypeptide chain), most often single chain Fv antibodies (sFv or scFv) in which a variable heavy and a variable light chain are joined together (directly or through a peptide linker) to form a continuous polypeptide. The single chain Fv antibody is a covalently linked $V_H$-$V_L$ heterodimer which may be expressed from a nucleic acid including $V_H$- and $V_L$- encoding sequences either joined directly or joined by a peptide-encoding linker. Huston, et al. (1988) Proc. Nat. Acad. Sci. USA, 85: 5879-5883. While the $V_H$ and $V_L$ are connected to each as a single polypeptide chain, the $V_H$ and $V_L$ domains associate non-covalently.

The first functional antibody molecules to be expressed on the surface of filamentous phage were single-chain Fv's (scFv), however, alternative expression strategies have also been successful. For example Fab molecules can be displayed on phage if one of the chains (heavy or light) is fused to g3 capsid protein and the complementary chain exported to the periplasm as a soluble molecule. The two chains can be encoded on the same or on different replicons; the important point is that the two antibody chains in each Fab molecule assemble post-translationally and the dimer is incorporated into the phage particle via linkage of one of the chains to g3p (see, e.g., U.S. Pat. No.: 5,733,743). The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (se,e e.g., U.S. Pat. Nos. 5,091,513, 5,132,405, and 4,956,778). Frequently used antibodies include all those that have been displayed on phage (e.g., scFv, Fv, Fab, and disulfide linked Fv (Reiter et al. (1995) Protein Eng. 8: 1323-1331). The term "antibody" also includes bivalent or bispecific molecules, miniantibodies, diabodies, triabodies, and tetrabodies. Bivalent and bispecific molecules are described in, e.g., Kostelny et al. (1992) *J Immunol* 148:1547, Pack and Pluckthun (1992) *Biochemistry* 31:1579, Hollinger et al., 1993, supra, Gruber et al. (1994) *J Immunol*:5368, Zhu et al. (1997) *Protein Sci* 6:781, Hu et al. (1996) *Cancer Res.* 56:3055, Adams et al. (1993) *Cancer Res.* 53:4026, and McCartney, et al. (1995) *Protein Eng.* 8:301.

As used herein "immunoglobulin variable region domain" refers to any $V_H$ or $V_L$ domain used as a binding moiety without a companion $V_H$ or $V_L$ domain. As with antibodies, such domains may be linked in various configurations to other polypeptide(s) that may perform various functions, e.g.,as responder, inhibitor, or reactivator.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 is located in the variable domain of the heavy chain of the antibody in which it is found, whereas a $V_L$ CDR1 is the CDR1 from the variable domain of the light chain of the antibody in which it is found. CDR and framework regions may be determined using various well known definitions, and are typically determined in accordance with Kabat (see, e.g., Johnson et al., (2001) "Kabat Database and its applications: future directions" *Nucleic Acids Research*, 29: 205-206; and the Kabat Database of Sequences of Proteins of Immunological Interest, Feb. 22, 2002 Dataset).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in Monoclonal Antibodies and Cancer Therapy (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

"Antigen" refers to substances which are capable, under appropriate conditions, of inducing a specific immune response and of reacting with the products of that response, that is, with specific antibodies or specifically sensitized T-lymphocytes, or both. Antigens may be soluble substances, such as toxins and foreign proteins, or particulates, such as bacteria and tissue cells; however, only the portion of the protein or polysaccharide molecule known as the antigenic determinant (epitopes) combines with the antibody or a specific receptor on a lymphocyte. More broadly, the term "antigen" may be used to refer to any substance to which an antibody binds, or for which antibodies are desired, regardless of whether the substance is immunogenic. For such antigens, antibodies may be identified by recombinant methods, independently of any immune response.

"Antibody library" refers to a repertoire or synthetic library of genes encoding antibodies or antibody fragments such as Fab, scFv, Fd, LC, $V_H$, or $V_L$, which is obtained from the natural ensemble, or "repertoire", of antibodies present in human donors, and obtained primarily from the cells of peripheral blood and spleen. In a preferred embodiment, the human donors are "non-immune", i.e., not presenting with symptoms of infection.

"Binding" refers to the non-covalent adherence of molecules to one another, for example, enzymes to substrates, antibodies to antigens, DNA strands to their complementary strands. Binding occurs because the shape and chemical natures of parts of the molecules surfaces are complementary.

"Binding affinity" is generally expressed in terms of equilibrium association or dissociation constants ($K_a$ or $K_d$, respectively), which are in turn reciprocal ratios of dissociation and association rate constants ($k_d$ and $k_a$, respectively). Thus, equivalent affinities may comprise different rate constants, so long as the ratio of the rate constants remains the same.

A "binding ensemble member" refers to a molecule that participates in a specific binding interaction with another member of the binding ensemble. A binding ensemble often comprises two members, i.e., a binding pair, but can comprise three or more members. For example, an antigen and two antibodies that recognize two different epitopes on the antigen and can be bound to the antigen at the same time comprise a binding ensemble. The "third" member, e.g., an antigen, brings the first and second members of the binding ensemble, e.g., two antibodies, into proximity. A third member of a binding ensemble need not be a single molecule, e.g., a single protein or polypeptide, but may comprise multiple subunits. The other members of the binding ensemble may therefore bind to either the same subunit or different subunits. For example, a cell and two antibodies that bind to two different epitopes on one cell surface protein or to two different cell surface proteins at the same time comprise a binding ensemble in which a "third" member, i.e., the cell, comprises multiple subunits. A "target binding ensemble member" is a molecule to which the binding molecule of interest, e.g., an antibody, specifically binds.

Binding ensemble members can include antibodies/antigens, receptors/ligands, biotin/avidin, and interacting protein domains such as leucine zippers. and the like, as well as components of supra-molecular structures such as ribosomes, transcription complexes, cytoskeletal structures, signal transduction complexes, and metabolic complexes. A binding ensemble member as used herein can be a binding domain, i.e., a subsequence of a protein that binds specifically to another member of the binding ensemble. In reference to binding pairs, the binding pair members can also be referred to as a binding pair member and a binding partner (or cognate binding partner). Binding ensembles can also include docking agents, i.e., members that are added to dock binding ensemble members to the responder and/or the inhibitor, or to the reactivator, such as, for example, biotin/avidin, antibody/antigen, or leucine zipper.

A "binding partner" refers to a molecule that specifically binds to another molecule. The binding interaction is often a direct interaction, but can also be an indirect interaction.

"Chimeric polynucleotide" means that the polynucleotide comprises regions which are wild-type and regions which are mutated. It may also mean that the polynucleotide comprises wild-type regions from one polynucleotide and wild-type regions from another related polynucleotide.

"Competitor" refers to that molecule whose binding to the antigen or target molecule in the systems of the invention leads to inhibition of the reporter. Thus, in the systems of the invention, test molecules must compete with the competitor for binding to the antigen or target molecule in order to activate the reporter and be selected.

A "complex" as used herein refers to an assemblage of components that are linked, either covalently or non-covalently, e.g., via a binding interaction. As appreciated by one of skill in the art, components that are linked by a binding interaction will typically be in an equilibrium, depending on the affinity and concentration of the components.

"Docking" and "dock" refer to a binding interaction between two molecules which brings other molecules into proximity, which other molecules are linked to the docking molecules.

"Domain" refers to a unit of a protein or protein complex, comprising a polypeptide subsequence, a complete polypeptide sequence, or a plurality of polypeptide sequences where that unit has a defined function. The function is understood to be broadly defined and can be binding to a binding partner, catalytic activity, structural activity, or can have a stabilizing effect on the structure of the protein. "Domain" also refers to a structural unit of a protein or protein complex, comprising one or more polypeptide sequences where that unit has a defined structure which is recognizable within the larger structure of the native protein. The domain structure is understood to be semi-autonomous in that it may be capable of forming autonomously and remaining stable outside the context of the native protein.

"Epitope" refers to that portion of an antigen or other macromolecule capable of forming a binding interaction that interacts with the variable region binding pocket of an antibody. Typically, such binding interaction is manifested as an intermolecular contact with one or more amino acid residues of a CDR.

The term "expression vector" includes vectors which are capable of expressing nucleic acid sequences contained therein, i.e., any nucleic acid sequence which is capable of effecting expression of a specified nucleic acid code disposed therein (the coding sequences are operably linked to other sequences capable of effecting their expression). Some expression vectors are replicable in the host organism either as episomes or as an integral part of the chromosomal DNA. A useful, but not a necessary, element of an effective expression vector is a marker encoding sequence—i.e. a sequence encoding a protein which results in a phenotypic property (e.g. tetracycline resistance) of the cells containing the protein which permits those cells to be readily identified. Expression vectors are frequently in the form of plasmids or viruses. However, the invention is intended to include such other forms of expression vectors which serve equivalent functions and which may, from time to time become known in the art.

"Heterologous", when used with reference to portions of a protein, indicates that the protein comprises two or more domains that are not found in the same relationship to each other in nature. Such a protein, e.g., a fusion protein or a conjugate protein, contains two or more domains from unrelated proteins arranged to make a new functional protein. Heterologous may also refer to a natural protein when it is found or expressed in an unnatural location such as when a mammalian protein is expressed in a bacterial cell.

"Homologs" means polypeptides having the same or conserved residues at a corresponding position in their primary, secondary or tertiary structure. The term also extends to two or more nucleotide sequences encoding the homologous polypeptides. Example homologous peptides are the immunoglobulin isotypes.

"Idiolog" is an antibody which shares its antigen and epitope specificity with another antibody, e.g., a reference antibody, but which is not derived from that antibody.

An "inhibitor" refers to a molecule that can inhibit the activity of the responder.

A "low-affinity inhibitor" is a relative term referring to an embodiment of the inhibitor where the inhibitor has a $K_d$ (equilibrium dissociation constant) for the responder which is at least ten-fold higher than the working concentration of the inhibitor, such that the inhibitor cannot bind to the responder to an appreciable extent without a heterologous mechanism for bringing the two together.

As used herein "interaction" refers generally to attractive physical interactions, i.e., the binding of two or more molecules into a supra-molecular complex which is stable in the sense that each component has an affinity for at least one other member of the complex corresponding to a $K_d$ of $\leq 1$ mM.

The term "interaction" or "interacts" when referring to the interaction of binding ensemble members generally refers to binding to one another. However, it may also refer to indirect interaction mediated by other molecules, usually additional binding ensemble members. Accordingly, a molecule that interferes with the binding interaction of binding ensemble members with one another decreases or prevents binding of a binding ensemble member to another member of the binding ensemble. Typical binding pairs include antibodies/antigens, receptor/ligands, subunits of multimeric proteins or supra-molecular structures. "Binding" or "interacting" as used herein refers to noncovalent associations, e.g., hydrogen bonding, ionic bonding, electrostatic bonding, hydrophobic interaction, Van der Waals associations, and the like.

The term "library of expressed sequences" refers to any population of nucleotide sequences which are derived from messenger RNA, and which are therefore understood to encode polypeptide sequences, or fragments thereof, that are produced naturally in cells.

As used herein "ligand" refers to a molecule that is recognized by, i.e., binds to, a particular receptor. As one of skill in the art will recognize, a molecule (or macromolecular complex) can be both a receptor and a ligand, typically when both are soluble or both are membrane-bound. However, when one is membrane-bound and the other is soluble, the former is commonly referred to as the receptor and the latter is the ligand. When both are soluble, the binding partner having a smaller molecular weight is typically referred to as the ligand and the binding partner having a greater molecular weight is referred to as a receptor. More generally, the binding partners of non-receptor proteins may also be referred to as ligands. A "mutagenized" natural ligand is a variant of a ligand that retains binding activity. An "artificial non-antibody ligand" is a nonnaturally occurring ligand that specifically binds to a binding partner.

A "linker" or "spacer" refers to a molecule or group of molecules that covalently connects two molecules, such as a binding pair member and a responder or an inhibitor, and serves to place the two molecules in a preferred configuration, e.g., so that a responder can interact with an activator or inhibitor with minimal steric hindrance from a binding pair member, and a binding pair member can bind to a binding partner with minimal steric hindrance from the responder or inhibitor. A "flexible linker" refers to a peptide linker of any length in which the amino acid composition minimizes the formation of rigid structure by interaction of amino acid side chains with each other or with the polypeptide backbone. Typically a "flexible linker" is rich in glycine. An example of such a linker has the composition $(Gly_4Ser)_x$, where "x" may typically vary from 1 to 10.

"Link" or "join" or "fuse" refers to any method of functionally connecting peptides, typically covalently, including, without limitation, recombinant fusion of the coding sequences, and covalent bonding (e.g., disulfide bonding). In the systems of the invention, a binding pair member is typically linked or joined or fused, often using recombinant techniques, at the amino-terminus or carboxyl-terminus by a peptide bond to a responder or to an activator or inhibitor of the responder. However, the binding pair member may also be inserted into the responder or inhibitor at an internal location that can accept such insertions. The binding pair member can either directly adjoin the fragment to which it is linked or fused or it can be indirectly linked or fused, e.g., via a linker sequence. "Linked" may also refer to a non-covalent physical association, particularly one which is constitutive, i.e., does not require docking, under operating conditions. For example, in a responder mixture comprised of responder, inhibitor, and binding ensemble member, each component is typically linked to at least one other component, either covalently, e.g., via peptide linkage, or non-covalently, via high-affinity binding interaction.

A "member" or "component" in the context of a responder system refers to a responder, a fragment or subsequence of a responder, a subunit of a responder, or an activator or inhibitor of the responder. The responder can be a complete polypeptide, or a fragment or subsequence thereof that retains responder activity.

The term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame.

"Recombinant nucleic acid" refers to a nucleic acid in a form not normally found in nature. That is, a recombinant nucleic acid is flanked by a nucleotide sequence not naturally flanking the nucleic acid or has a sequence not normally found in nature. Recombinant nucleic acids can be originally formed in vitro by the manipulation of nucleic acid by restriction endonucleases, or alternatively using such techniques as polymerase chain reaction. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention.

"Recombinant polypeptide" refers to a polypeptide expressed from a recombinant nucleic acid, or a polypeptide that is chemically synthesized in vitro.

"Recombinant variant" refers to any polypeptide differing from naturally occurring polypeptides by amino acid insertions, deletions, and substitutions, created using recombinant DNA techniques. Guidance in determining which amino acid residues may be replaced, added, or deleted without abolishing activities of interest, such as enzymatic or binding activities, may be found by comparing the sequence of the particular polypeptide with that of homologous peptides and minimizing the number of amino acid sequence changes made in regions of high homology.

Preferably, amino acid "substitutions" are the result of replacing one amino acid with another amino acid having similar structural and/or chemical properties, i.e., conservative amino acid replacements. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

"Insertions" or "deletions" are typically in the range of about 1 to 5 amino acids. The variation allowed may be experimentally determined by systematically making insertions, deletions, or substitutions of amino acids in a polypeptide molecule using recombinant DNA techniques and assaying the resulting recombinant variants for activity.

Alternatively, where alteration of function is desired, insertions, deletions or non-conservative alterations can be engineered to produce altered polypeptides. Such alterations can, for example, alter one or more of the biological functions or biochemical characteristics of the polypeptides of the invention. For example, such alterations may change polypeptide characteristics such as ligand-binding affinities, interchain affinities, or degradation/turnover rate. Further, such alterations can be selected so as to generate polypeptides that are better suited for expression, scale up and the like in the host cells chosen for expression. For example, cysteine residues can be deleted or substituted with another amino acid residue in order to eliminate disulfide bridges.

Alternatively, recombinant variants encoding these same or similar polypeptides may be synthesized or selected by making use of the "redundancy" in the genetic code. Various codon substitutions, such as the silent changes which produce various restriction sites, may be introduced to optimize cloning into a plasmid or viral vector or expression in a particular prokaryotic or eukaryotic system. Mutations in the polynucleotide sequence may be reflected in the polypeptide or domains of other peptides added to the polypeptide to modify the properties of any part of the polypeptide, to change characteristics such as ligand-binding affinities, interchain affinities, or degradation/turnover rate.

A "reference antibody" is a known antibody for which the practitioner wants to obtain a variant with improved binding characteristics, e.g., higher binding affinity.

A "reference binding molecule" is a molecule that binds a binding partner for which the practitioner wants to obtain a variant with improved binding characteristics, e.g., higher binding affinity.

The term "responder" refers to any protein that produces a detectable signal, including, but not limited to detectable signals such as fluorescence, enzymatic activity, a selectable phenotype (e.g., antibiotic resistance), a screenable phenotype, or that produces an activity that results in a phenotypic change or provides a functional product that is detectable.

The term "reporter" as used herein, refers to a responder that produces a detectable signal, or that confers a selectable phenotype.

A "scaffolded peptide" refers to a peptide, typically of up to about 20 amino acids in length, that is inserted into a natural protein at a location known to accept such insertions without interfering with the folding or native configuration of the protein (A Skerra, *J Mol Recognit* 13:167-87, 2000). Usually the location is on the surface of the protein. Often, the peptide is not a known natural sequence, and therefore is not expected to fold into a stable structure on its own, but generally assumes a random coil structure in solution. However, when inserted into the scaffold protein the peptide is expected to acquire some degree of stable structure by packing against the surface of the protein. Such structure generally improves the ability of the peptide to bind with high affinity to other molecules, such as other proteins. Many proteins may serve as scaffolds for random peptide libraries. Frequently, surface loops between elements of secondary structure such as α-helixes or strands of a β-sheet may accept such insertions without significant perturbation of folding or structure. Examples of proteins that have been used as scaffolds include, but are not limited to, thioredoxin (or other thioredoxin-like proteins), nucleases (e.g., RNase A), proteases (e.g., trypsin), protease inhibitors (e.g., bovine pancreatic trypsin inhibitor), antibodies or structurally-rigid fragments thereof, and other domains of the immunoglobulin superfamily.

"Synthetic antibody library" refers to a library of genes encoding one or more antibodies or antibody fragments such as Fab, scFv, Fd, LC, VH, or VL, in which one or more of the complementarity-determining regions (CDR) has been partially or fully randomized by oligonucleotide-directed mutagenesis. "Randomized" means that part or all of the sequence encoding the CDR has been replaced by sequence randomly encoding all twenty amino acids or some subset of the amino acids.

"Test antibody" or "candidate antibody" refers to a variant of the reference antibody. The "test antibody" is typically a member of a library of variants that usually bind the same epitope. Similarly, a "test molecule" or "candidate molecule" refers to a binding molecule that analyzed for improved affinity for a binding partner relative to the reference binding molelule.

Introduction

The current invention provides methods of generating binding molecules with improved binding properties, e.g., affinity, relative to a starting reference binding molecule. In many embodiments, the methods identify affinity matured antibodies. Although the invention may be described in terms of antibodies, one of skill in the art understands that any number of other binding molecules, e.g., ligands, peptides, or other binding proteins, can also be affinity matured using the same techniques.

The methods involve the use of responder systems in which responder activity is influenced by the presence of an improved antibody, or other binding molecule, e.g., one with a higher binding affinity, which thus provides a basis for identifying the improved binding ensemble member. Test antibody, antigen, and components of the responder systems are co-expressed with a competitor such that responder activation becomes dependent on the ability of the test antibody to compete with the competitor, which is proportional to the affinity of the test antibody for the antigen. Accordingly, in the affinity maturation techniques of the invention, each cell typically expresses a single test antibody, along with the competitor, antigen, and responder components so that each test antibody competes individually with the competitor for binding to limiting antigen. The activity of the responder molecule is proportional to the amount of antigen bound to the test antibody, which in turn is proportion to the affinity and stability of the test antibody. Repeated rounds of competition using a competitor selected for improved binding, e.g., affinity, in the previous round allows identification of test antibodies with significantly improved binding in comparison to the starting antibody.

The responder systems are of two types, reactivation systems and competitive activation systems. A reactivation system (RAIR system) involves two complexes, one containing a responder, an inhibitor and a binding ensemble member (the responder complex) and the other comprising a reactivator and a binding ensemble member (the reactivator complex). The responder is inhibited via the action of the inhibitor in its complex. A binding interaction, either direct or indirect, between the binding ensemble members in the responder complex and reactivator complex brings the reactivator into proximity such that the reactivator displaces the inhibitor from the responder. For affinity maturation, the system is configured such that the presence of an antibody with improved affinity leads to reactivation in the presence of a competitor molecule such as a reference binding pair member. For example, the reporter-inhibitor fusion and the reactivator of an auto-inhibited reporter may be fused to antigen and test antibody and used to select antigen-binding antibodies in the presence of competitors.

Alternatively, a competitive activation system (COMPACT™) may be used. This involves a responder molecule that is linked to one binding ensemble member; and an inhibitor of the responder molecule that is linked to another binding ensemble member. Interaction of the binding ensemble members results in inhibition of responder activity. Such a system may further employ a mask to provide added sensitivity. For example, a reporter and inhibitor of a competitive activation system may be linked to antigen and competitor so that the reporter is inhibited by antigen-competitor binding and activated in the presence of any test antibody that competes with the competitor for antigen binding.

The COMPACT™ and RAIR systems employ conjugate molecules that are generated in vivo by recombinant expression. COMPACT™ and RAIR systems are described, e.g., in co-pending U.S. application Ser. No. 10/076,845, filed Feb. 14, 2002, and Ser. No. 10/208,730, filed Jul. 29, 2002.

General Methods

The conjugates included in the systems of the invention are protein molecules that are produced by recombinant expression of nucleic acids encoding the proteins as a fusion protein. Expression methodology is well known to those of skill in the art. Such a fusion product can be made by ligating the appropriate nucleic acid sequences encoding the desired amino acid sequences to each other by methods known in the art, in the proper reading frame, and expressing the product by methods known in the art (see, e.g., Scopes, *Protein Purification: Principles and Practice*, Springer-Verlag, New York 1994; Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. New York, 1997).

Nucleic acids encoding the domains to be incorporated into the fusion proteins of the invention can be obtained using routine techniques in the field of recombinant genetics (see, e.g., Sambrook and Russell, eds, *Molecular Cloning: A Laboratory Manual*, 3rd Ed, vols. 1-3, Cold Spring Harbor Laboratory Press, 2001; and *Current Protocols in Molecular Biology*, Ausubel, ed. John Wiley & Sons, Inc. New York, 1997).

Often, the nucleic acid sequences encoding the component domains to be incorporated into the fusion protein are cloned from cDNA and genomic DNA libraries by hybridization with probes, or isolated using amplification techniques with oligonucleotide primers. Amplification techniques can be used to amplify and isolate sequences from DNA or RNA (see, e.g., Dieffenbach & Dveksler, *PCR Primers: A Laboratory Manual* (1995)). Alternatively, overlapping oligonucleotides can be produced synthetically and joined to produce one or more of the domains. Nucleic acids encoding the component domains can also be isolated from expression libraries using antibodies as probes.

In an example of obtaining a nucleic acid encoding a domain to be included in the conjugate molecule using PCR, the nucleic acid sequence or subsequence is PCR amplified, using a sense primer containing one restriction site and an antisense primer containing another restriction site. This will produce a nucleic acid encoding the desired domain sequence or subsequence and having terminal restriction sites. This nucleic acid can then be easily ligated into a vector containing a nucleic acid encoding the second domain and having the appropriate corresponding restriction sites. The domains can be directly joined or may be separated by a linker, or other, protein sequence. Suitable PCR primers can be determined by one of skill in the art using the sequence information provided in GenBank or other sources. Appropriate restriction sites can also be added to the nucleic acid encoding the protein or protein subsequence by site-directed mutagenesis. The plasmid containing the domain-encoding nucleotide sequence or subsequence is cleaved with the appropriate restriction endonuclease and then ligated into an appropriate vector for amplification and/or expression according to standard methods.

Examples of techniques sufficient to direct persons of skill through in vitro amplification methods are found in Berger, Sambrook, and Ausubel, as well as Mullis et al., (1987) U.S. Pat. No. 4,683,202; *PCR Protocols A Guide to Methods and Applications* (Innis et al., eds) Academic Press Inc. San Diego, Calif. (1990) (Innis); Arnheim & Levinson (Oct. 1, 1990) *C&EN* 36-47; *The Journal Of NIH Research* (1991) 3: 81-94; (Kwoh et al. (1989) *Proc. Natl. Acad. Sci. USA* 86: 1173; Guatelli et al. (1990) *Proc. Natl. Acad. Sci. USA* 87, 1874; Lomell et al. (1989) *J. Clin. Chem.*, 35: 1826; Landegren et al., (1988) *Science* 241: 1077-1080; Van Brunt (1990) *Biotechnology* 8: 291-294; Wu and Wallace (1989) *Gene* 4: 560; and Barringer et al. (1990) *Gene* 89: 117.

In some embodiments, it may be desirable to modify the polypeptides encoding the components of the conjugate molecules. One of skill will recognize many ways of generating alterations in a given nucleic acid construct. Such well-known methods include site-directed mutagenesis, PCR amplification using degenerate oligonucleotides, exposure of cells containing the nucleic acid to mutagenic agents or radiation, chemical synthesis of a desired oligonucleotide (e.g., in conjunction with ligation and/or cloning to generate large nucleic acids) and other well-known techniques. See, e.g., Giliman and Smith (1979) *Gene* 8:81-97, Roberts et al. (1987) *Nature* 328: 731-734.

For example, the domains can be modified to facilitate the linkage of the two domains to obtain the polynucleotides that encode the fusion polypeptides of the invention. Catalytic domains and binding domains that are modified by such methods are also part of the invention. For example, a codon for a cysteine residue can be placed at either end of a domain so that the domain can be linked by, for example, a disulfide linkage. The modification can be performed using either recombinant or chemical methods (see, e.g., Pierce Chemical Co. catalog, Rockford Ill.).

The domains of the recombinant fusion proteins are often joined by linkers, usually polypeptide sequences of neutral amino acids such as serine or glycine, that can be of varying lengths, for example, about 200 amino acids or more in length, with 1 to 100 amino acids being typical. Often, the linkers are 10, 15, 20, 25, 30, 35, 40, 45, or 50 amino acid residues or less in length. In some embodiments, proline residues are incorporated into the linker to prevent the formation of significant secondary structural elements by the linker. Linkers can often be flexible amino acid subsequences that are synthesized as part of a recombinant fusion protein. Such flexible linkers are known to persons of skill in the art. Typically, a flexible linker is a peptide linker of any length whose amino acid composition is rich in glycine to minimize the formation of rigid structure by interaction of amino acid side chains with each other or with the polypeptide backbone. A typical flexible linker has the composition $(Gly_4Ser)_x$.

In some embodiments, the recombinant nucleic acids encoding the fusion proteins of the invention are modified to provide preferred codons which enhance translation of the nucleic acid in a selected organism (e.g., yeast preferred codons are substituted into a coding nucleic acid for expression in yeast).

Expression Cassettes and Host Cells for Expressing the Fusion Polypeptides

There are many expression systems for producing the fusion polypeptide that are well know to those of ordinary skill in the art. (See, e.g., *Gene Expression Systems*, Fernandes and Hoeffler, Eds. Academic Press, 1999.) Typically, the polynucleotide that encodes the fusion polypeptide is placed under the control of a promoter that is functional in the desired host cell. An extremely wide variety of promoters are available, and can be used in the expression vectors of the invention, depending on the particular application. Ordinarily, the promoter selected depends upon the cell in which the promoter is to be active. Other expression control sequences such as ribosome binding sites, transcription termination sites, enhancers, operators, and the like are also optionally included. Constructs that include one or more of these control sequences are termed "expression cassettes."

Accordingly, the nucleic acids that encode the joined polypeptides are incorporated for the desired level of expression in a desired host cell.

Expression control sequences that are suitable for use in a particular host cell are often obtained by cloning a gene that is expressed in that cell. Commonly used prokaryotic control sequences, which are defined herein to include promoters for transcription initiation, optionally with an operator, along with ribosome binding site sequences, include such commonly used promoters as the β-lactamase (penicillinase) and lactose (lac) promoter systems (Change et al., *Nature* (1977) 198: 1056), the tryptophan (trp) promoter system (Goeddel et al., *Nucleic Acids Res.* (1980) 8: 4057), the tac promoter (DeBoer, et al., *Proc. Natl. Acad. Sci. U.S.A.* (1983) 80:21-25); and the lambda-derived $P_L$ promoter and N-gene ribosome binding site (Shimatake et al., *Nature* (1981) 292: 128). The particular promoter system is not critical to the invention, any available promoter that functions in prokaryotes can be used. Standard bacterial expression vectors include plasmids such as pBR322-based plasmids, e.g., PBLUESCRIPT™, pSKF, pET23D, λ-phage derived vectors, p15A-based vectors (Rose, *Nucleic Acids Res.* (1988) 16:355 and 356) and fusion expression systems such as GST and LacZ. Epitope tags can also be added to recombinant proteins to provide convenient methods of isolation, e.g., c-myc, HA-tag, 6-His tag, maltose binding protein, VSV-G tag, anti-DYKDDDDK tag, or any such tag, a large number of which are well known to those of skill in the art.

For expression of fusion polypeptides in prokaryotic cells other than *E. coli*, regulatory sequences for transcription and translation that function in the particular prokaryotic species is required. Such promoters can be obtained from genes that have been cloned from the species, or heterologous promoters can be used. For example, the hybrid trp-lac promoter functions in *Bacillus* in addition to *E. coli*. These and other suitable bacterial promoters are well known in the art and are described, e.g., in Sambrook et al. and Ausubel et al. Bacterial expression systems for expressing the proteins of the invention are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available.

Similarly, for expression of fusion polypeptides in eukaryotic cells, transcription and translation sequences that function in the particular eukaryotic species are required. For example, eukaryotic expression systems for mammalian cells, yeast, and insect cells are well known in the art and are also commercially available. In yeast, vectors include Yeast Integrating plasmids (e.g., YIp5) and Yeast Replicating plasmids (the YRp series plasmids) and pGPD-2. Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A+, pMTO10/A+, pMAM-neo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Either constitutive or regulated promoters can be used in the present invention. Regulated promoters can be advantageous because the concentration of heterologous protein in the host cell can be controlled. An inducible promoter is a promoter that directs expression of a gene where the level of expression is alterable by environmental or developmental factors such as, for example, temperature, pH, anaerobic or aerobic conditions, light, transcription factors and chemicals.

For *E. coli* and other bacterial host cells, inducible promoters are known to those of skill in the art. These include, for example, the lac promoter, the bacteriophage lambda $P_L$ promoter, the hybrid trp-lac promoter (Amann et al. (1983) *Gene* 25: 167; de Boer et al. (1983) *Proc. Nat'l. Acad. Sci. USA* 80: 21), and the bacteriophage T7 promoter (Studier et al. (1986) *J. Mol. Biol.*; Tabor et al. (1985) *Proc. Nat'l. Acad. Sci. USA* 82: 1074-8). These promoters and their use are discussed in Sambrook et al., supra.

Inducible promoters for other organisms are also well known to those of skill in the art. These include, for example, the metallothionein promoter, the heat shock promoter, as well as many others.

Translational coupling may be used to enhance expression. The strategy uses a short upstream open reading frame derived from a highly expressed gene native to the translational system, which is placed downstream of the promoter, and a ribosome binding site followed after a few amino acid codons by a termination codon. Just prior to the termination codon is a second ribosome binding site, and following the termination codon is a start codon for the initiation of translation. The system dissolves secondary structure in the RNA, allowing for the efficient initiation of translation. See Squires, et. al. (1988), *J. Biol. Chem.* 263: 16297-16302.

In some embodiments it may be desirable to include a signal peptide to target the expressed product to a particular location, e.g., a bacterial periplasmic space. Such signal polypeptides are known in the art.

The construction of polynucleotide constructs generally requires the use of vectors able to replicate in host bacterial cells, or able to integrate into the genome of host bacterial cells. Such vectors are commonly used in the art. A plethora of kits are commercially available for the purification of plasmids from bacteria (for example, EasyPrepJ, FlexiPrepJ, from Pharmacia Biotech; StrataCleanJ, from Stratagene; and, QIAexpress Expression System, Qiagen). The isolated and purified plasmids can then be further manipulated to produce other plasmids, and used to transform cells.

The fusion polypeptides can be expressed intracellularly, or can be secreted from the cell. Intracellular expression often results in high yields. If necessary, the amount of soluble, active fusion polypeptide may be increased by performing refolding procedures (see, e.g., Sambrook et al., supra.; Marston et al., *Bio/Technology* (1984) 2: 800; Schoner et al., *Bio/Technology* (1985) 3: 151). Fusion polypeptides of the invention can be expressed in a variety of host cells, including *E. coli*, other bacterial hosts, yeast, and various higher eukaryotic cells such as the COS, CHO and HeLa cells lines and myeloma cell lines. The host cells can be mammalian cells, insect cells, or microorganisms, such as, for example, yeast cells, bacterial cells, or fungal cells.

Once expressed, the recombinant fusion polypeptides can be purified according to standard procedures of the art, including ammonium sulfate precipitation, affinity columns, column chromatography, gel electrophoresis and the like (see, generally, R. Scopes, *Protein Purification*, Springer-Verlag, N.Y. (1982), Deutscher, *Methods in Enzymology Vol. 182: Guide to Protein Purification.*, Academic Press, Inc. N.Y. (1990)). Substantially pure compositions of at least about 90 to 95% homogeneity are preferred, and 98 to 99% or more homogeneity are most preferred.

To facilitate purification of the fusion polypeptides of the invention, the nucleic acids that encode the fusion polypeptides can also include a coding sequence for an epitope or "tag" for which an affinity binding reagent is available.

Examples of suitable epitopes include the myc and V-5 responder genes; expression vectors useful for recombinant production of fusion polypeptides having these epitopes are commercially available (e.g., Invitrogen (Carlsbad Calif.) vectors pcDNA3.1/Myc-His and pcDNA3.1/V5-His are suitable for expression in mammalian cells). Additional expression vectors suitable for attaching a tag to the fusion proteins of the invention, and corresponding detection systems are known to those of skill in the art, and several are commercially available (e.g., FLAG" (Kodak, Rochester N.Y.). Another example of a suitable tag is a polyhistidine sequence, which is capable of binding to metal chelate affinity ligands. Typically, six adjacent histidines are used, although one can use more or less than six. Suitable metal chelate affinity ligands that can serve as the binding moiety for a polyhistidine tag include nitrilo-tri-acetic acid (NTA) (Hochuli, E. (1990) "Purification of recombinant proteins with metal chelating adsorbents" In Genetic Engineering: Principles and Methods, J. K. Setlow, Ed., Plenum Press, NY; commercially available from Qiagen (Santa Clarita, Calif.)).

One of skill would recognize that modifications can be made to the protein domains without diminishing their biological activity. Some modifications may be made to facilitate the cloning, expression, or incorporation of a domain into a fusion protein. Such modifications are well known to those of skill in the art and include, for example, the addition of codons at either terminus of the polynucleotide that encodes the binding domain to provide, for example, a methionine added at the amino terminus to provide an initiation site, or additional amino acids (e.g., poly His) placed on either terminus to create conveniently located restriction sites or termination codons or purification sequences Modification of polypeptide domains to produce variants may also be performed. A "variant" has used herein refers to a version of the polypeptide of interest that has been mutated. Typically, a population of variants is produced in order to select a version of the polypeptide of interest that has an enhanced property relative to the parent, e.g., increased binding affinity. Thus, a variant specifically binds the same binding partner as the parent binding pair member. Methods of introducing mutations are well known in the art (see, e.g., Sambrook and Ausubel, supra). For example, error-prone PCR or chemical mutagenesis can be performed to introduce mutations. In some embodiments, it may be desirable to introduce mutations at particular sites and then select for the enhanced property. In such instances, techniques such as site-specific mutagenesis may be performed.

Affinity Maturation Systems of the Invention

Responders

Responders include any protein that produces a detectable signal, a selectable phenotype, or which performs a useful function in response to the interaction of binding ensemble members. For example, enzymes such as β-lactamase may be used to generate a color signal from chromogenic or fluorogenic substrates, or to confer an antibiotic resistance phenotype on host bacterial cells, or to activate a cephalosporin prodrug to produce a cancer-killing drug upon interaction with, i.e., binding to a cancer marker. Other enzymes that can be used as responder proteins include those that hydrolyze chromogenic or fluorogenic substrates to yield a colored or fluorescent product. These include, for example, β-galactosidase, alkaline phosphatase, peroxidases, esterases, carboxypeptidases, glycosidases, glucuronidases, and carbamoylases. Still other useful enzymes are listed in U.S. Pat. No. 6,220,964 (which is incorporated by reference), and include penicillin-amidases, aminoglycoside phosphotransferases, e.g., neomycin phosphotransferase, puromycin N-acetyltransferase (Sanchez-Puig et al., Gene 257:57-65, 2000, incorporated by reference), and chloramphenicol acetyl transferase.

Non-enzymatic molecules can also be employed as responders using the methods of the invention. For example, biological response modifiers, such as insulin, can be used to activate useful cellular functions, such as glucose uptake in insulin-dependent diabetics, in response to the presence of subject molecules, such as glucose. Fluorescent proteins such as the green fluorescent protein (GFP) of Aequorea Victoria (Chalfie et al., (1994) Science 263: 802-805) can also be employed as responders. GFP absorbs blue light and fluoresces green. GFP fluorescence can be quenched or shifted in cis by fusing it to a protein or other molecule that perturbs the chromophore. Reactivators can be fashioned from proteins or other molecules that bind to the quencher/shifters, thereby preventing them from binding to GFP.

Further examples of responder molecules can be found in U.S. Pat. Nos. 6,294,330; 6,220,964; 6,342,345; and/or U.S. patent application Ser. No. 09/526,106, filed on Mar. 15, 2000.

Reactivation Systems

As previously stated, supra, reactivation-based molecular interaction systems can be used in the invention to select/screen for antibodies having desired properties. In general, reactivation-based molecular interaction systems are comprised of responders, inhibitors, reactivators, and binding ensembles of two or more members. The system has two complexes, one containing the responder, the inhibitor, and a binding ensemble member (the responder complex), and the other containing the reactivator and a binding ensemble member (the reactivator complex).

Molecular interaction between the first and the second ensemble members can be detected by the following mechanism: the signal or activity of the responder in the responder complex is greatly diminished or extinguished by the inhibitor present in the complex, i.e., the responder is auto-inhibited; when a reactivator complex is introduced, if the second ensemble member in the reactivator complex binds with sufficient affinity to the first ensemble member in the responder complex, the reactivator will be able to displace the inhibitor from the responder complex and lead to the so-called "reactivation of an auto-inhibited responder." The detection of responder activity or signal indicates an interaction between the first and the second ensemble members.

Reactivators can be readily fashioned from responders by mutagenically disabling responder activity without disabling inhibitor binding. Usually, a single mutation is sufficient. However, any molecule that competes with the responder for binding to the inhibitor can also be used as a reactivator.

Variations of the RAIR systems can be used for improving the affinity of a first binding pair member. In some variations, a third ensemble member may be used.

Reactivation system components and methods of making the reactivation systems are disclosed in U.S. patent application Ser. No. 10/208,730.

Competitive Activation Systems

Systems using molecular sensors activated by competition (COMPACT™) can also be used in the invention to select/screen for binding molecules, e.g., antibodies having improved affinity. In general, competitive activation systems are comprised of a binding ensemble, a responder, and an inhibitor. The responder is complexed with one binding ensemble member and the inhibitor is complexed to another binding ensemble member. The binding ensemble members, upon binding to one another, bring the responder and inhibitor together so that the responder is inhibited. In affinity maturation applications, binding molecules, e.g., antibodies, that disrupt the binding ensemble or inhibit binding ensemble formation and thereby activate the responder can be selected. In one embodiment, the binding ensemble is an antibody(s) and an antigen(s), and the "competitive activator" is an antibody. For example, the binding ensemble antibody might be a reference antibody, and the competitive activator may comprise a library of antibodies which compete with the reference for binding to the antigen. Competitive activation system components and methods of making the systems are disclosed in U.S. patent application Ser. No. 10/076,845.

In some embodiments, a competitive activation system may employ a "mask" (also described in U.S. application Ser. No. 10/076,845) to control the sensitivity of the system. A "mask", in the context of a competitive activation system, refers to a molecule that has low affinity for a reporter or inhibitor, such that the mask does not bind appreciably at working concentrations unless it is tethered covalently to the reporter or inhibitor. The mask does not affect reporter activity only the binding of the inhibitor and vice versa. Control of the system with masks permits a high-affinity inhibitor to be used without increasing the background inhibition because its association rate constant is greatly reduced by the mask without affecting the dissociation rate constant of the reporter-inhibitor complex, thereby reducing the overall affinity while retaining the stability of the high-affinity reporter-inhibitor complex.

Competitors

The systems and the methods of the invention include a competitor in the selection system to drive affinity selection. In many embodiments, the competitor is the reference binding molecule, e.g., reference antibody, i.e., a known antibody for which the practitioner wants to obtain a higher affinity analog. As used herein, an analog binds to the same site on a binding partner, e.g., the antigen, as the reference binding molecule, but does not have the identical sequence at its binding site.

As understood by one in the art, cell-based affinity maturation is a reiterative process, wherein the highest-affinity test binding molecule selected in a given round becomes the reference binding molecule for the next round. Generally, the competitor for the next round will be identical to the reference molecule. However, the reference molecule may be modified for use as competitor by. For example, a reference antibody may be modified as a competitor by retaining only the exact binding domain of the reference antibody and expressing it without further modification. The competitor binding molecule may be fused to other domains which may confer desirable properties on the competitor, such as stability.

Competitors can be provided to the cell population in which the affinity maturation occurs in a number of ways. For example, the competitor can be encoded on a separate expression vector or can be included as a discistronic component along with the cognate binding partner fusion protein. Competitors can also be constituitively present in the host cell or otherwise provided, e.g., inducibly expressed.

In antibody applications, competitors are typically antibody competitors, but are not limited to antibody competitors. For example, peptides or other molecules that share a binding property with the reference antibody can be used in the methods of the invention.

Antibody Competitors

Antibody competitors can be in the form of Fab, scFv, Fv, dab, Fd fragments, single heavy chain v-region domains ($V_H$), single light chain v-region domains ($V_L$), light chain-light chain antibody, heavy chain-heavy-chain antibody, and single light chains or heavy chains. In one embodiment, the compositions of the invention comprise a plurality of antibodies individually complexed to a component of an interaction system. In some embodiments, the competitor is a chimeric, or hybrid, antibody. Such an antibody can have one antibody chain frame a reference antibody and a second antibody chain from a different source. In a preferred embodiment, the plurality of antibodies is a library of antibodies having a desired level of diversity.

In a typically selection system, each cell expresses a single test antibody along with the competitor, antigen, and reporter components, so that each test antibody competes one-on-one with the competitor for binding to limiting antigen, and the activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of test antibodies which differ from the reference antibody in having one or more mutations, and at least one of which selected test antibodies has higher affinity for the antigen than that of the reference antibody.

In the second and subsequent rounds, the antibodies selected in the first or previous round may also be used as competitors. The result of the second and any subsequent round of selection is a set of antibodies which differ from the those of the previous round in having one or more additional mutations, and at least one of which selected test antibodies has higher affinity for the antigen than the best of the previous round.

On-rate and Off-rate Selection

"Affinity" generally refers to the equilibrium association constant ($K_a$), which determines how much of an antibody is bound to an antigen at equilibrium. However, the affinity is equivalent to the ratio of association and dissociation rate constants ($k_a$, "on-rate" and $k_d$, "off-rate"). This means that different pairs of on-rate and off-rate constants can have the same affinity as long as they have the same ratio, but their binding kinetics can be very different. For example, an antibody with a high on-rate and high off-rate may have the same affinity as one with a low on-rate and low off-rate, but initially it will bind to free antigen much faster. For many applications of antibodies, the importance of on-rate and off-rate are not equivalent. Thus, having the right affinity may not be enough. It may be more important that the affinity be comprised of the right on-rate and the right off-rate. For example, a therapeutic antibody may only need to be bound to its target for a few minutes before its work is done, but the faster it binds the better. Thus, it does not need an off-rate of less than $10^{-3}$ $\text{sec}^{-1}$, but the higher the on-rate the better. This means that an antibody with a $10^{-3} \text{ sec}^{-1}$ off-rate and a $10^6 M^{-1} \text{sec}^{-1}$ on-rate would be up to 100-fold more effective than an antibody with a $10^{-5} \text{ sec}^{-1}$ off-rate and a $10^4 M^{-1} \text{sec}^{-1}$ on-rate, even though they both have the same affinity. On the other hand, when the bioactivity of a therapeutic antibody is limited by the rates of auxiliary activities, i.e., effector functions, and not by the binding kinetics of the antibody, the half-life of the antigen-antibody complex, determined by the off-rate, becomes more important than the rate of formation of the antigen-antibody complex, determined by the on-rate.

In general, it is important that any scheme for affinity maturation allow selection for balanced increments in both on-rate and off-rate to ensure that the right property is improved. Any scheme that allows independent selection for on-rate and off-rate improvements has the distinct advantage that the correct property can be improved most efficiently. Display methods are the only current antibody selection methods which are suitable for affinity maturation (Hoogenboom et al., *Immunotechnology* 4:1-20, 1998), apart from the current invention. With display methods, balanced off-rate and on-rate selections can only be accomplished using equilibrium conditions (Hawkins et al., *J. Mol. Biol.* 226:889-896, 1992), which require such low concentrations of antigen and antibody for enrichment of rare, high-affinity clones that recovery of such clones is exceedingly difficult. Independent off-rate selection is more reliable, but on-rate selection is definitely not practical with display methods. The RAIR™ and COMPACT™ systems, on the other hand, allow for a substantial measure of balanced as well as independent selection for improvements in both on-rates and off-rates where needed.

In affinity maturation applications with RAIR systems, the reporter-inhibitor fusion and the reactivator may be fused to antigen and test antibody in either pairing and in either orientation, depending on which configuration supports the greatest specific reactivation of the reporter upon antigen-test antibody binding. When the test antibody and antigen complexes are co-expressed with a competitor, reporter activation depends on the ability of the test antibody to compete with the competitor, which is proportional to the affinity of the test antibody for the antigen. Competition in RAIR systems actually occurs on two levels, and this allows for somewhat independent selection for higher association rate constants ($k_a$, "on-rate") and/or lower dissociation rate constants ($k_d$, "off-rate"). Competitor and test antibody compete for binding to antigen primarily on the basis of their respective on-rates, conferring a selective advantage on test antibodies having higher on-rates. However, reactivation of the auto-inhibited reporter also requires that the off-rate of the test antibody-antigen complex be substantially lower than that of the reporter-inhibitor complex in the auto-inhibited reporter. Otherwise, the antigen-test antibody complex will dissociate before the reactivator has a chance to bind to the inhibitor. Thus, if an inhibitor variant is used in the auto-inhibited reporter, which has a lower off-rate than that of the reference antibody-antigen complex, such that the reference antibody, when used as the test antibody, would be unable to reactivate the reporter. Under this condition, only test antibodies having lower off-rates than that of the reference antibody can activate the reporter and be selected. This condition can actually be used without a competitor for a pure off-rate selection. However, retention of the competitor in the selection minimizes the possibility that lower off-rates with reduced on-rates can be selected. For off-rate selections with RAIR systems, it is extremely useful to have a series of reporter inhibitor variants having different off-rates.

Affinity maturation with balanced on-rate and off-rate improvements can also be accomplished with competitive activation systems, e.g., COMPACT™. In these systems the reporter and inhibitor are linked to antigen and competitor in either pairing and in either orientation, depending on which configuration supports the greatest specific inhibition of the reporter upon antigen-competitor binding. In the presence of any test antibody that competes with the competitor for antigen binding at a higher affinity, docking of the inhibitor is prevented and the reporter is activated. As in the RAIR systems, the competitor and test antibodies compete for binding to the antigen primarily on the basis of on-rate, conferring a selective advantage on test antibodies having higher on-rates. However, due to the avidity of the competitor-antigen complex in the COMPACT™ system, which is comprised of the combined affinities of competitor-antigen and reporter-inhibitor, this complex may not dissociate appreciably during the lifetime of the proteins once it is formed. Thus, the competitor-antigen complex is, in effect, a sink for reporter activity, and the rate at which the reporter is drawn into the sink is controlled by the off-rate of the test antibody, conferring a selective advantage on test antibodies with lower off-rates. The lower the test antibody off-rate, the more slowly the reporter will be drawn into the sink, and the higher the steady-state reporter activity. In this way the system allows selection for both lower off-rates as well as for higher on-rates.

Library of Candidate Binding Molecules

The library of candidate binding molecules can be any number of libraries, e.g., a randomly generated library of test binding pair members. Often the library is a mutagenized library. The library of test binding pair members can be generated using a variety of mutagenesis methods including, for example, error-prone PCR (Cadwell and Joyce, in *PCR Primer, A Laboratory Manual*, Dieffenbach and Dveksler, Eds. Cold Spring Harbor Press, Cold Spring Harbor N.Y., pp. 583-590, 1995), Parsimonious Mutagenesis (PM) (Balint and Larrick, *Gene* 137:109-118, 1993), DNA shuffling (Crameri et al., *Nature Biotechnol.* 14:315-19, 1996), random-priming recombination (RPR) (Shao et al., *Nucleic Acids Res.* 26:681-683, 1998), or the staggered extension process (StEO) (Zhao et al, *Nature Biotechnol.* 16:258-261, 1998). For these methods, except PM, it is typically desirable to have a mutation rate of 1-3 mutations per clone to avoid unwanted mutations. For PM, higher mutation rates can be used because only the protein combining sites of the binder are mutagenized. PM may therefore be advantageous for accessing larger affinity increments. PM has additional advantages in avoiding folding mutants, avoiding immunogenicity, and ease of sequencing.

The library can be expressed using vectors and expression systems known in the art. In some embodiments, the library vector is a phagemid.

Examples of the uses of the techniques are provided in the context of generating antibody libraries, but the techniques can also be applied to making libraries of other candidate binding molecules.

In reference to antibody libraries, an expression library includes DNA sequences that encode the epitope-binding portions of heavy- and light-chain variable regions of immunoglobulin (Ig); see, e.g., Marks, *J. Biol. Chem.* 267: 16007-10, 1992; Griffiths, *EMBO J.* 12: 725-734, 1993. Alternatively, the displayed protein can be a single-chain (scFv) Ig fragment (see, e.g., Pistillo *Exp. Clin. Immunogenet.* 14:123-130, 1997.

The diversity of binding sites for a group or library of antibodies is a reflection of the diversity of sequence in the CDRs, the degree of combinatorial combinations of these CDRs in the light and heavy chains, and the degree of combinatorial combinations of the light and/or heavy chains in a group or library of antibodies. All three of these variables may be manipulated to generate a group or library of antibodies having a desired level of diversity. Methods for generating antibody binding diversity are disclosed, for example, in U.S. Pat. No. 6,096,551.

For example, the diversity of an antibody library can be increased by shuffling the heavy and light chain genes (Kang et al., *Proc. Nat'l Acad. Sci.* 88:11120-11123 (1991)), or by altering the CDRs of the cloned antibody genes (Barbas et al., Proc. Nat'l Acad. Sci. 89:4457-4461 (1992); Gram et al., Proc. Nat'l Acad. Sci. 89:3576-3580 (1992)).

Mutagenesis of the CDRs can be done by error-prone replication, replicative incorporation of degenerate oligonucleotides, or by the methods of chemical or UV mutagenesis. These methods are well-known in the art and are disclosed, for example, in Sambrook et al. and Ausubel et al.

PCR may also be used to create amino acid sequence variants of the polynucleotides of the invention. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide or protein at the position specified by the primer. The product DNA fragments replace the corresponding region in the plasmid and this gives the desired amino acid variant. In another embodiment, error prone PCR may be used to generate amino acid variants in the polynucleotides that encode the antibodies.

In another method, polynucleotides encoding the antibodies of the invention are changed via site-directed mutagenesis. This method uses oligonucleotide sequences that encode the polynucleotide sequence of the desired amino acid variant, as well as a sufficient adjacent nucleotide on both sides of the changed amino acid to form a stable duplex on either side of the site of being changed. In general, the techniques of site-directed mutagenesis are well known to those of skill in the art and this technique is exemplified by publications such as, Edelman et al., *DNA* 2:183 (1983). A versatile and efficient method for producing site-specific changes in a polynucleotide sequence was published by Zoller and Smith, *Nucleic Acids Res*. 10:6487-6500 (1982). PCR may also be used to create amino acid sequence variants of the novel nucleic acids. When small amounts of template DNA are used as starting material, primer(s) that differs slightly in sequence from the corresponding region in the template DNA can generate the desired amino acid variant. PCR amplification results in a population of product DNA fragments that differ from the polynucleotide template encoding the polypeptide at the position specified by the primer. The product DNA fragments replace the corresponding region in the plasmid and this gives the desired amino acid variant.

A further technique for generating amino acid variants is the cassette mutagenesis technique described in Wells et al., *Gene* 34:315 (1985); and other mutagenesis techniques well known in the art, such as, for example, the techniques in Sambrook et al., supra, and *Current Protocols in Molecular Biology*, Ausubel et al. Due to the inherent degeneracy of the genetic code, other DNA sequences which encode substantially the same or a functionally equivalent amino acid sequence may be used in the practice of the invention for the cloning and expression of these novel nucleic acids. Such DNA sequences are capable of hybridizing to the appropriate novel nucleic acid sequence under stringent conditions.

Shuffling of the CDRs within an antibody polypeptide chain may be accomplished by techniques which are well known in the art. U.S. Pat. Nos. 6,096,551 and 6,372,497 teach exemplary methods for shuffling antibody CDRs.

The light chains and heavy chains, light chains and light chains, or heavy chains and heavy chains may be combinatorial combined to produce the desired level of binding diversity within the antibody library. U.S. Pat. Nos. 5,885,793, 6,300,064, and 6,096,551 teach exemplary methods for "shuffling" antibody chains to increase diversity.

Parsimonious mutagenesis as disclosed in Balint et al. *Gene* 137(1):109-18 (1993), is a method for maximizing binding diversity in an antibody library with a minimal number of changes within the CDRs. This method creates libraries with low-redundancy 'doping' codons and biased nucleotide mixtures designed to maximize the abundance of combining sites with predetermined proportions of preselected sets of alternative amino acids. This allows the library to 'probe' the surface of the antigen one or a few amino acid residues at a time with a wide selection of amino acid side chains to search out and identify new high-affinity contacts.

Culture Conditions for Affinity Selection

The affinity maturation procedures disclosed herein take place in a bacterial cell, typically a gram negative bacterium such as *E. coli*. In a preferred embodiment, affinity maturation involves assembly of the binding ensembles within the periplasm of a bacteria. In some applications, it is desirable to modify the oxidative state of the periplasm.

The secretory compartment of gram-negative bacteria, i.e., the periplasmic space, has many similarities to the secretory compartments of eukaryotic cells, thus it is a useful environment for functional expression and cell-based selection of antibodies, particularly for secreted antigens, which are the majority of therapeutic targets. The only serious drawback of the bacterial periplasm is its oxidizing power, which is much stronger than that of the eukaryotic endoplasmic reticulum. As a result, when eukaryotic proteins are translocated into the periplasmic space, they often do not fold fast enough to avoid the formation of non-native disulfide bonds by the potent oxidase, DsbA, which arrests folding. Such disulfides can be reduced by reductases to allow folding to continue, but this often does not occur fast enough to save heterologous proteins from aggregation or proteolysis.

The periplasmic expression of many eukaryotic proteins can be substantially improved by including thiol reagents such as reduced glutathione, dithiothreitol, N-acetyl cysteine, or -mercaptoethanol in the growth medium (e.g., see U.S. patent application Ser. No. 09/764,163). These reagents diffuse readily into the periplasm and interact with the DsbA enzyme, thereby competitively reducing its activity toward protein thiols. For example, reduced glutathione may be included in the medium at concentrations ranging up to 5 mM before it becomes toxic. Within this range, soluble periplasmic expression increases steadily for a variety of heterologous proteins, including human and murine antibody single-chain Fv fragments, VH domains, VL domains, Fab fragments, other immunoglobulin-like domains such as the CD86 receptor, other receptors such as CD40, CD40 ligand, and the epidermal growth factor receptor (EGFR), and non-secreted proteins such as calmodulin. Thus, most eukaryotic proteins, particulary secreted proteins, can be functionally expressed, at least at moderate levels, in the *E. coli* periplasm by including, when necessary, a sulfhydryl reagent in the medium at an optimal concentration, which can be empirically determined.

Selection is desirably performed under optimized conditions. Optimization can be performed by considering a number of factors, including the optimization of the negative control. A negative control is established that is typically the maximum affinity one wishes to exclude from selection, i.e., that of the binder to be improved. Thus, for the negative control, the binding molecule to be improved is expressed not solely as the competitor but also as the reference binding molecule, in place of the test binding pair members. Several conditions are generally taken into consideration for optimal selection: (1) the antigen or binding ensemble member is limiting, preferably no more than about one-tenth the concentration of the competitor, in order to force competition between the competitor and the test binding pair members, (2) the competitor is in excess over a concentration equal to its $K_d$, preferably 10-fold, so that the binding partner is at least 90% competitor-bound in the negative control, and (3) the test binding pair member concentration should be comparable to that of the binding partner, i.e., no more than about 10% that of the competitor, so that the negative control has not more than about 10% of the maximum reporter activity. This provides a dynamic ranges of a factor of about 10.

Control of Levels of Expression of System Components

The levels of expression are typically controlled to achieve desirable relative levels of expression of the components of the system. Suitable conditions can be achieved, for example, by manipulating the configuration of the expression vectors and selecting suitable promoters. For example, particular components can be expressed from a dicistronic transcript from a strong promoter such as the trp-lac fusion promoter. Translation of the upstream cistron is typically more efficient than that of the downstream cistron. In such conditions, a competitor encoded by the upstream cistron would be present in excess. Other members of the system can be expressed from a weaker promoter such as the lac operon promoter in a separate, compatible vector. This will provide a method for controlling expression levels of the various components.

If such expression conditions are not optimal for a given antigen-antibody pair, additional manipulations are available to further control the expression levels of one or more of the components. For example, if competitor expression is weak, stronger promoters, e.g., the bacteriophage T7 promoter, are available.

If expression of any component is too strong, or if proportions among the components are not suitable, inducible promoters can be used, such as the arabinose operon promoter, which allows the expression level of any of the components to be manipulated to an appropriate level.

In order to evaluate overall levels of expression of the components of a system, the amount of polypeptide produced by the expression vectors can be determined using assays such as immunoblots. In practice, the levels of expression of the components of the system are established empirically in a negative control, supra, based on the considerations identified above.

Uses of the Methods and Systems of the Invention

Affinity maturation can be used in a number of applications to generate higher affinity binding pair members. For example, the methods and systems of the invention can be used to generate superior antibodies or human antibodies corresponding to a mouse counterpart. The techniques can also be used to identify peptides that have a higher binding affinity, e.g., peptides that are improved agonists or antagonists for a receptor, or for any other application for which a binding peptide with enhanced affinity is desirable. Small molecules with enhanced binding affinity for a target can also be identified, e.g., using a biotin tag system.

Therapeutic Antibody Development

In one application, the systems and methods of the invention can be used to develop therapeutic antibodies. Affinity maturation can mold low-affinity antibody combining sites into rigid shapes with high complementarity to epitope surfaces. Therefore, the starting libraries do not have to be particularly large or diverse. For example, a library can be built on a single-chain Fv platform comprising a single pair of well-expressing human germline VH and VL regions with random sequences inserted into the CDR3 of VH and VL. Such a library can be made efficiently by ligating synthetic oligonucleotides containing random sequences to appropriate restriction endonuclease sites engineered into the antibody coding sequence. A library of about $10^8$ such sequences typically has enough diversity to produce antibodies of micromolar affinity in the methods of the invention.

An additional advantage of a single-platform library is that the antibody expression levels are typically uniform. Structural diversity among the antibodies is limited to the surface of the protein, and therefore has little impact on either the folding kinetics or the stability of the antibodies. Furthermore, e.g., in the PM method for mutagenesis, mutations can be limited to the CDRs and are therefore less likely to affect expression levels.

For therapeutic applications, important performance parameters for antibodies include specificity, stability, lack of immunogenicity, and the on-rate. For most antibody targets in vivo the off-rate does not need to be lower than $10^{-3}$-$10^{-4}$ sec$^{-1}$, which corresponds to half-lives of 11 min to 2 hours. Most surface-bound antibodies either undergo endocytosis or engage in effector functions such as phagocytosis or complement fixation within this time frame. However, there is no identified upper limit beyond which further increases in the on-rate are not therapeutically advantageous. Thus, the invention described herein can provide superior antibodies for therapeutic applications. If it is advantageous to use full-length antibodies of specific isotypes for therapeutic applications, linkers present in affinity matured antibodies can be removed and the required constant regions added to the scFvs.

EXAMPLES

Example 1

Affinity Maturation of an Antibody using a Target-mediated β-lactamase Competitive Activation System This example demonstrates the utility of the invention for affinity maturation by demonstrating the selection of a higher-affinity variant of an antibody from a million-fold excess of the parent antibody. A schematic of the general procedure is provided in FIG. 1.

The antibody used for this example was a mouse monoclonal raised against the extra-cellular domain of the human B-cell activation antigen CD40, and isolated by hybridoma technology. This antibody, designated HB15, had a $K_d$ for CD40 of 7.6 nM, as determined by surface plasmon resonance (Fägerstam et al. (1992) J Chromatog 597: 397-410). A higher-affinity variant of this antibody was subsequently identified which contained two mutations in the third complementarity-determining region (CDR3) of the heavy chain variable region (Vl), which conferred a 12-fold increase in the affinity of the antibody. This variant was designated HB15Y.

Figure 2:
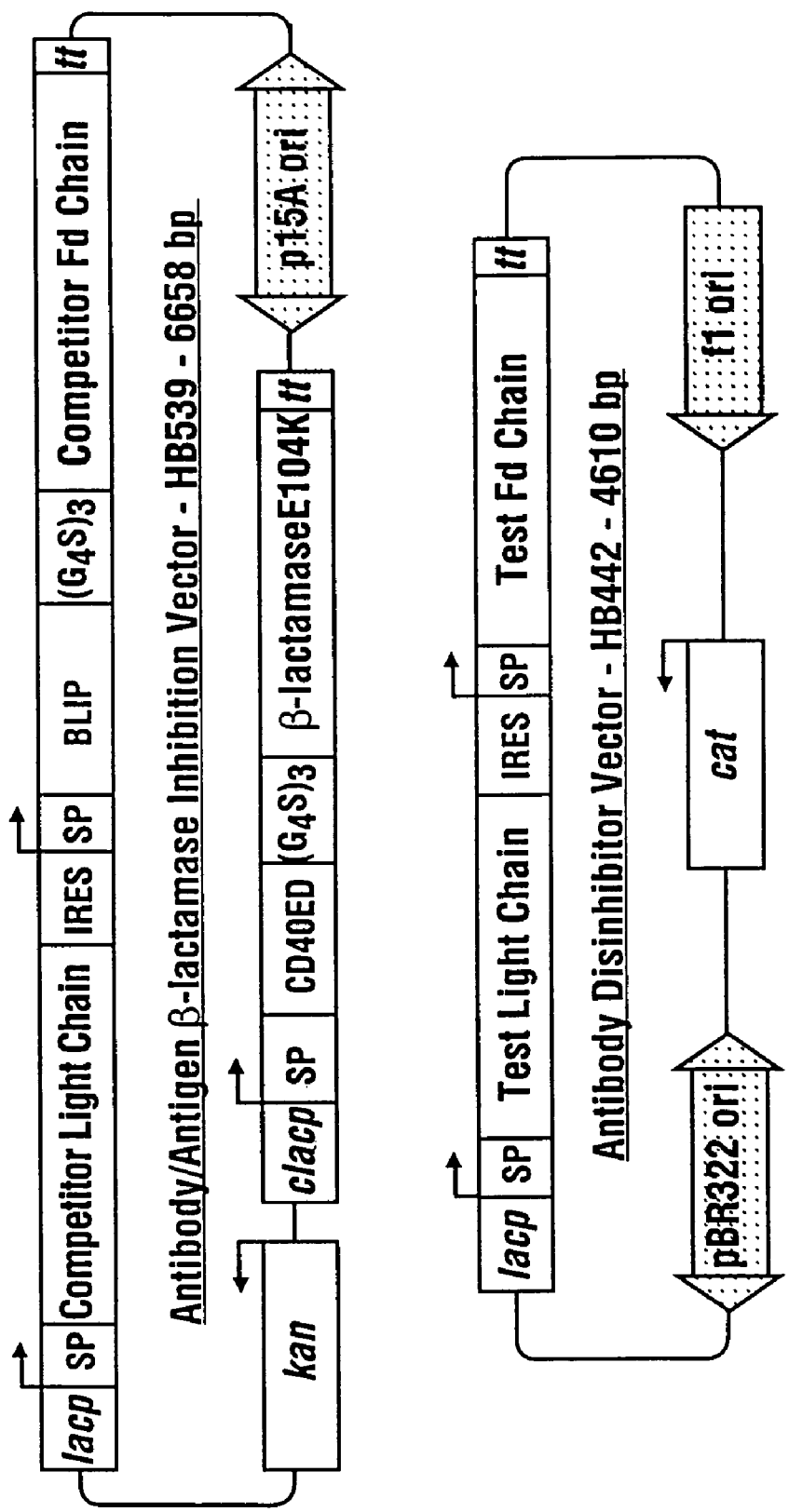
FIG. 2 shows exemplarly expression vectors for antigen-antibody interaction-mediated inactivation of β-lactamase and for antibody-mediated activation of β-lactamase by competitive activation. Antibodies are expressed as Fabs (LC plus Fd) from dicistronic transcripts. IRES, internal ribosome entry site for re-initiation of translation on the downstream cistron. This embodiment includes, a "competitor" molecule, i.e., the Fab against which the "test" Fabs must compete for binding to the antigen in order to activate the reporter. The antigen in Example 1 is CD40ED, the extra-cellular domain of the human B-cell activation antigen CD40.

The vectors for expression of the system components for CD40-HB15 interaction-mediated inhibition of β-lactamase and activation by antibody-mediated competitive activation are depicted in FIG. 2. The CD40—β-lactamaseE104K fusion was expressed from a constitutive mutant of the lacUV5 promoter in the p15A vector denoted HB539. The HB15 antibodies were expressed in Fab form, i.e., VH-CH1 (Fd) with full-length light chain (LC). The Fabs were expressed from dicistronic transcripts driven by the lacUV5 promoter. The upstream cistron encoded the LC, followed by a ribosome binding site (IRES) to allow translation to re-initiate on the downstream cistron, which encoded the Fd fragment. The parent HB15 Fab (competitor) was fused to BLIP at the amino terminus of its Fd fragment via (Gly$_4$Ser)$_3$ linker, and expressed from the HB539 vector. The test Fabs were expressed from the pBR322 vector denoted HB442.

A Fab against an irrelevant antigen, i.e., glutathione S-transferase (GST), was used as a negative control. Table II presents data on the ability of these various Fabs to inactivate β-lactamaseE104K by docking BLIP thereto, and on their ability to competitively activate antibody-inhibited β-lactamase. Whereas, host cells expressing the GST Fab as the competitor, i.e., fused to BLIP, plated with 100% efficiency on ampicillin up to 200 μg/ml, the plating efficiency of cells expressing HB15 dropped steadily to <1 colony per 100,000 cells plated on 200 μg/ml ampicillin, indicating specific docking of BLIP to β-lactamase E104K by the HB15-CD40 interaction. The HB15Y mutant, as competitor did not plate appreciably better than the parent HB15, in spite of having a ~12-fold higher affinity. This indicates that the working concentrations of these antibodies in the cells are well above their $K_d$s, thus affinity is not limiting for β-lactamase inactivation. The same would be true for affinity selection using any interaction-mediated activation system. Thus, non-competitive selection for affinity can only succeed when working concentrations of the antibody are at or below the target $K_d$s, such that affinity remains limiting for the selectable phenotype. For affinity selection at lower target $K_d$s competition must be used between parent and mutant antibodies to allow the affinity of the mutants to be limiting for selectability.

Fab, and $10 \times 10^6$ cells of the mixed population were plated on 100 μg/ml ampicillin. As expected, at least 10,000 colonies were recovered. These colonies were scraped off the plates, resuspended in fresh medium, and quantified by light scattering optical density at 600 nm. The cells were then replated on 100 μg/ml ampicillin at ~10 cells per original colony, i.e., 100,000 cells total. From these cells 116 colonies were recovered. By PCR and signature sequencing, 44 of these colonies were found to be expressing the HB15Y test Fab, 61 were expressing the HB15 reference Fab, and the remainder appeared to have genetic rearrangements of one sort or another giving rise to false positives. Thus, in just two platings the frequency of the higher-affinity variant had increased from $10^{-6}$ to nearly one in two. This clearly demonstrates the utility of β-lactamase activation by competitive activation for antibody affinity maturation, and by extension, for affinity maturation of any binding molecule.

Example 2

Affinity Maturation of an Antibody using a Cellular Selection System Based on Competitive Reactivation of an Auto-inhibited Reporter (RAIR)

This example illustrates the use of a RAIR system for antibody affinity maturation. The auto-inhibited reporter is

TABLE II

Antibody Affinity Selection by Competitive Activation of β-lactamase[a.]

| | | | Ampicillin (μg/ml) | | | | |
|---|---|---|---|---|---|---|---|
| Competitor Fab | Test Fab | Test Fab $K_d$ | 10 | 25 | 50 | 100 | 200 |
| GST (neg. control) | — | NA | 100% | 100% | 100% | 100% | 100% |
| HB15 | — | NA | 100% | 45% | 1% | 0.01% | <0.001% |
| HB15Y | — | NA | 100% | 20% | 2% | 0.007% | <0.001% |
| HB15 | GST | — | 100% | 15% | 4% | 0.02% | <0.001% |
| HB15 | HB15 | 7.6 nM | 100% | 100% | 100% | 0.2% | 0.01% |
| HB15 | HB15Y | 0.6 nM | 100% | 100% | 80% | 100% | 0.6% |

[a.]*E. coli* cells expressing the constructs of FIG. 2 comprising the coding sequences of the indicated Competitor Fabs and Test Fabs were plated on solid medium containing the indicated concentrations of ampicillin. The data are expressed as % plating efficiency, i.e., % of doubly transformed cells plated which produced colonies after overnight growth at 33° C. The Fab-BLIP fusion and the Test Fab competitive activators require IPTG for expression.

Cells expressing HB15 as the competitor and GST Fab as the test antibody did not plate appreciably better than with no test antibody, confirming the inability of the GST Fab to compete with HB15 for binding to CD40. However, when HB15 itself was expressed as both competitor and test antibody, in which case it is referred to as the "reference binding pair member", plating efficiency was substantially increased, up to 25-fold on 50 μg/ml ampicillin, confirming that the CD40—β-lactamase fusion was limiting for competition between the competitor and test antibodies. When the higher-affinity HB15Y variant was used as the test antibody against the parent HB15 competitor, the plating efficiency increased still further compared to the reference antibody. Thus, the plating efficiency of the HB15Y test antibody reached a maximum of 500-fold higher than that of the reference (HB15) on 100 μg/ml ampicillin.

The foregoing results suggest that in a mixed population of test antibodies, the HB15Y test Fab should be enriched 500-fold relative to the reference antibody after each plating. To test this, cells expressing the HB15Y test Fab were mixed with a $10^6$-fold excess of cells expressing the HB15 reference comprised of a responder protein (also referred to in this example as a reporter protein) and an inhibitor of the reporter that are linked genetically so that the reporter is in a constitutively inhibited state. The system further comprises a reactivator protein that binds to the inhibitor competitively with the reporter and with an affinity that is at least comparable to that of the reporter, but which is not high enough to displace the inhibitor from the reporter when the reactivator and the auto-inhibited reporter are not physically linked. However, when the auto-inhibited reporter and the reactivator are each linked to molecules that interact with one another, such as an antibody and an antigen, that interaction brings the auto-inhibited reporter and the reactivator into close proximity, whereupon the inhibitor r e-equilibrates between the reporter and the reactivator, causing the detectable activation of the reporter.

Figure 3:
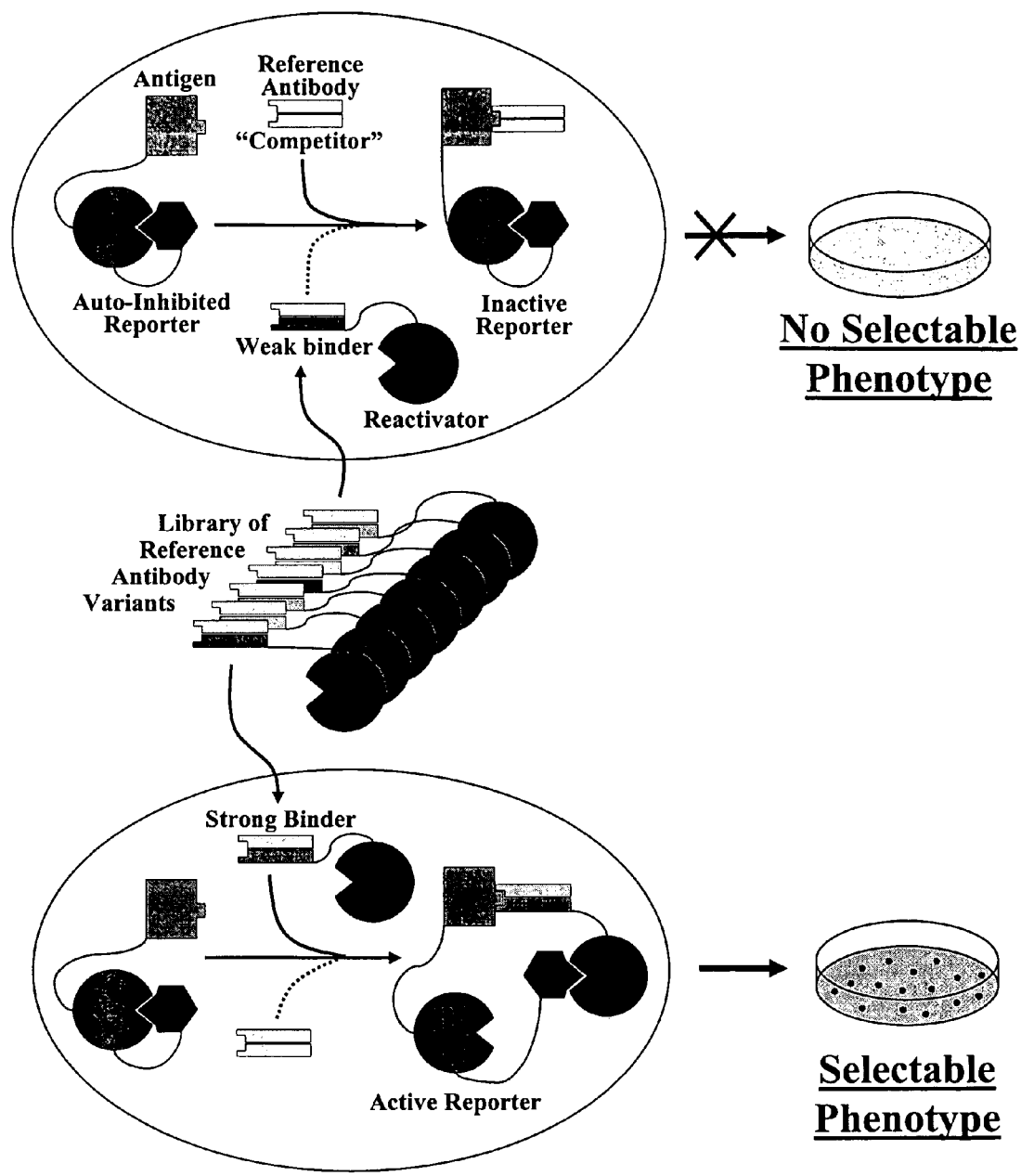
FIG. 3 illustrates the process of affinity maturation of an antigen-specific antibody using a cell-based selection system based on reactivation of an auto-inhibited reporter.

When the auto-inhibited reporter fusion and the reactivator fusion are co-expressed in cells, and when the reporter confers a selectable phenotype on the cells, such as antibiotic resistance, the antigen-antibody interaction can be monitored by the phenotype of the cells. When the antibody is a library of candidate antigen-binders, the selectable phenotype can be used to identify bona fide antigen-binders in the library. However, if the expression levels of the fusion proteins required for detectable phenotype are higher than the desired equilibrium dissociation constant ($K_d$) corresponding to the minimum desired affinity of the antigen-antibody interaction, then reporter activation will not be limited by the affinity of the interaction, and antigen-binding antibodies cannot be distinguished from one another by their affinities. For example, $K_d$s in the sub-nanomolar range are typically desired for antibodies, but such concentrations of signaling molecules in cells are usually not sufficient to generate robust phenotypes. Thus, when the antibody library is a library of candidate higher-affinity variants of the antibody, and the goal is to find the highest affinity variants, then it is necessary to disengage affinity from expression levels, so that reporter activation remains proportional to affinity at expression levels which are higher than the desired $K_d$ values. This is accomplished by setting up a competition in the cells between the library members and the reference antibody. Thus, for affinity maturation, the reference antibody is expressed as an unlinked "competitor" in each cell, along with the fusions of the library members and the antigen to the auto-inhibited reporter and reactivator. Each cell expresses a single library member that competes one-on-one in the cell with the reference antibody for binding to the antigen, so that the higher the affinity of a given library member, the more reactivator is docked to the auto-inhibited reporter, and the higher the reporter activity. Thus, the strength of the phenotype conferred by the reporter is proportional to the affinity of the library member. This is illustrated in FIG. 3.

Figure 4:
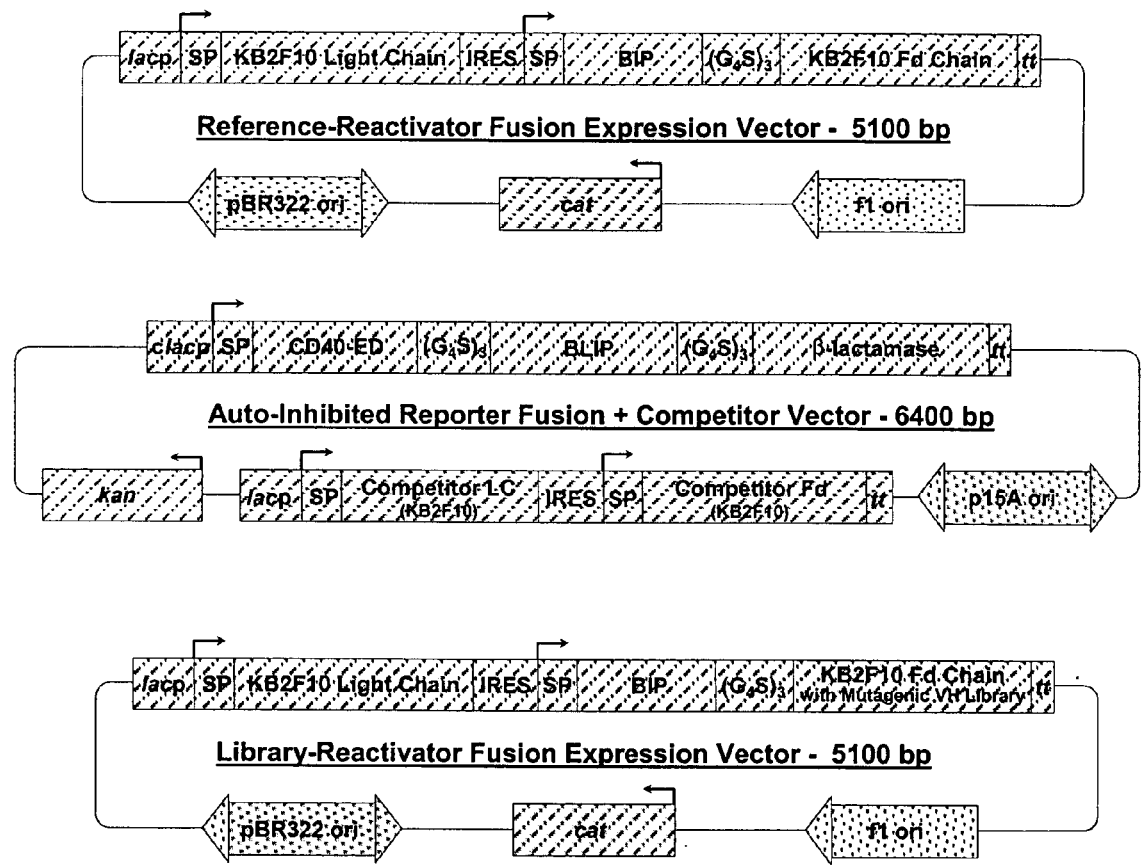
FIG. 4 shows vectors for expression of human CD40 and the anti-CD40 antibody KB2F10 as fusions to BLIP-inhibited β-lactamase and the reactivator BIP for affinity maturation of KB2F10 in Fab format. SP, signal peptide for secretion into the bacterial periplasm; lacp, lactose operon promoter; clacp, constitutive mutant of the lactose operon promoter; IRES, internal ribosome entry site, for translation of the downstream cistron in a dicistronic cassette; $(G_4S)_3$, flexible hydrophilic 15-mer linker comprised of $(Gly_4Ser)_3$; tt, transcription terminator; kan, kanamycin resistance gene; ori, origin of replication; fl ori, filamentous phage origin of replication for transformation by phage transfection; cat, chloramphenicol resistance gene.

The use of the β-lactamase RAIR system to improve the affinity of an antibody against the human CD40 antigen is described. Vectors for expression of the auto-inhibited reporter fusion protein, the reactivator fusion protein, and the reference antibody "competitor" in the *E. Coli* periplasm are illustrated in FIG. 4. The coding sequence of the human CD40 extra-cellular domain (CD40ED; Bajorath and Aruffo, 1997, Proteins: Struct, Funct, Genet 27:59-70) was recovered and amplified by RT-PCR from a commercial preparation of mRNA from peripheral blood lymphocytes, and inserted into the auto-inhibited reporter fusion vector for periplasmic expression of CD40 fused to the amino terminus of BLIP via $(Gly_4Ser)_3$ linker, which is in turn fused to β-lactamase via similar linker.

KB2F10 is a humanized murine antibody that binds the extra-cellular domain of human CD40 antigen. To establish optimum conditions for the selection of higher-affinity variants of KB2F10, the ability of KB2F10 to compete with itself for reactivation of β-lactamase in the RAIR system was determined. This establishes a threshold above which the stringency of selection has to be set in order to restrict the selection to only higher affinity variants. The variable region coding sequences of KB2F10 were subcloned into the reactivator fusion vector and into the competitor cassette in the reporter/competitor vector shown in FIG. 4 for expression as Fab fragments with human CH1 and CL constant regions to make the light chain and Fd chain. The Fabs in the two vectors are expressed from dicistronic transcripts. The order of cistrons is determined by which V-region is to be mutagenized. The chain which is common to the competitor and the library is expressed from the upstream cistron to ensure that it is in excess for the competing chains, so that the competing chains are competing for antigen and not for the common chain. Any of the six CDRs of the antibody may be affinity matured in any order. However, as the $V_H$ generally bears most of the binding affinity of an antibody, $V_H$ is generally mutagenizd first. Thus, the light chain is expressed from the upstream cistron and the Fd chain from the downstream cistron. For a negative competitor control, a non-binding Fab sequence was also inserted into the competitor cassette of the reporter/competitor vector, and for a negative test antibody control, the non-binding Fab sequence was inserted into the reactivator fusion cassette.

Figure 5:
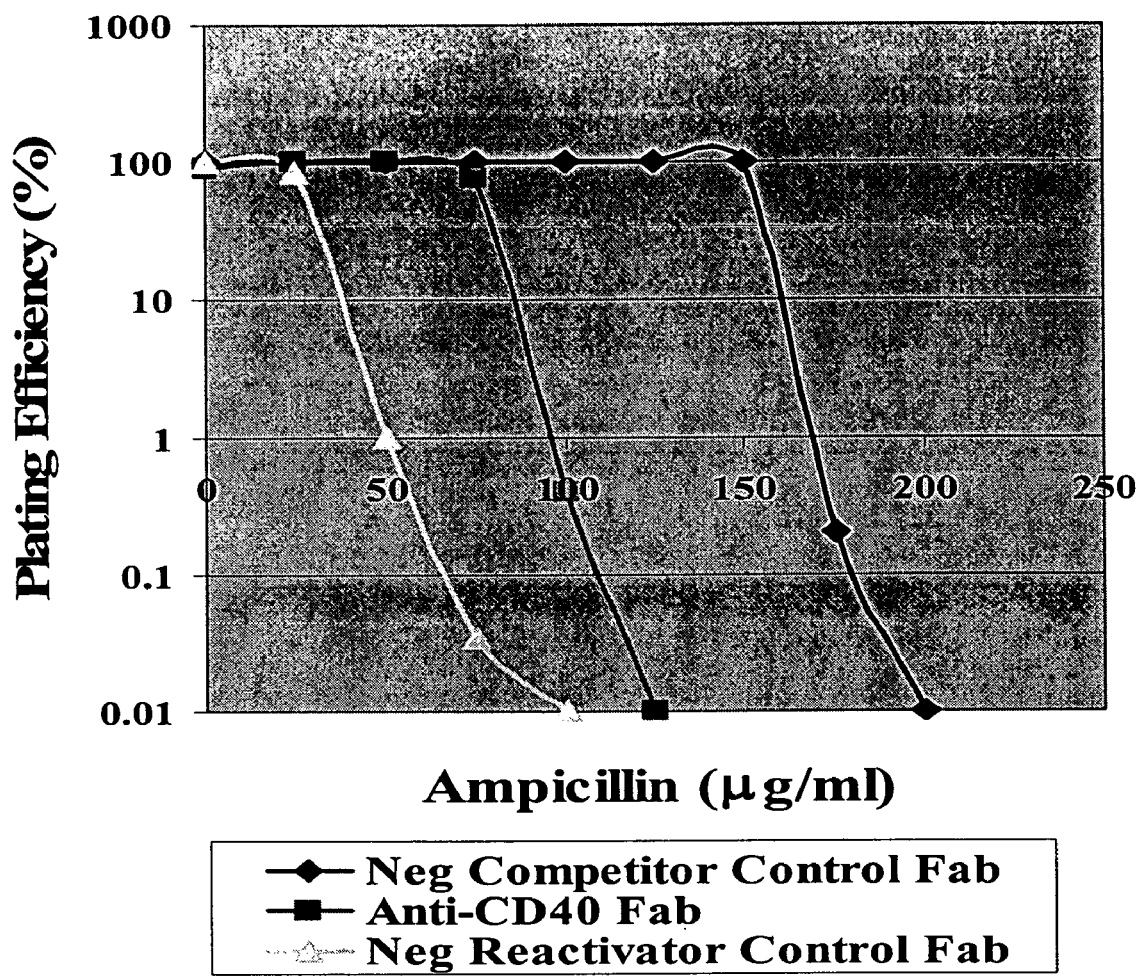
FIG. 5 shows graphs of plating efficiencies of *E. coli* cells expressing CD40-BLIP-β-lactamase fusion with various positive and negative antibody control constructs to establish optimum conditions for selection of higher-affinity variants of the KB2F10 antibody. In the positive control, the KB2F10 Fab is expressed as both the competitor and the test antibody fused to the reactivator, BIP. In the negative competitor control an anti-GST Fab was expressed instead of KB2F10. In the negative reactivator control, the anti-GST Fab was expressed instead of KB2F10 as the BIP fusion. Approximately 10,000 doubly transformed cells of each type (i.e., the positive and both negative controls) were seeded onto each of the indicated concentrations of ampicillin with several different concentrations of the antibody-reactivator fusion transcription inducer, IPTG, in solid 2×YT medium, and grown overnight at 33° C. Plating efficiencies were determined as the percentage of cells plated forming colonies, and plotted on a semi-log scale. Only the 50 µM IPTG data is shown.

Plasmid DNA of the Reference-Reactivator Fusion vector and the Reporter/Competitor vector (or each vector with a negative control vector of the other) were introduced simultaneously into *E. Coli* strain TOP10F' by high-voltage electroporation, and after a one-hour recovery, the cells were plated on solid rich medium (2×YT) containing increasing concentrations of the β-lactam antibiotic ampicillin which is hydrolyzed by β-lactamase. After overnight growth at 33° C. plating efficiencies (PE) were scored as the per cent of cells plated forming colonies. The results are shown in FIG. 5.

The two negative controls define the limits of the dynamic range. When there is no interaction between the reporter fusion and the reactivator fusion the PE declines rapidly above 25 μg/ml ampicillin. However, when there is no competitor, and an antibody-antigen interaction with affinity in the nanomolar $K_d$ range is driving reactivation of the auto-inhibited β-lactamase, the PE remains at 100% out to 150 μg/ml ampicillin. The latter condition would correspond roughly to one in which the test antibody would have a $K_d$ at least 10-fold lower than that of the competitor and both were expressed at comparable levels.

The test antibody-reporter fusion is expressed from an inducible promoter, which allows the expression of the reference antibody to be tuned to roughly the mid-point of the dynamic range. Since the relationship of test antibody affinity to PE is sigmoidal, this is the area of greatest sensitivity of the selection system, where the increase in PE per unit increase in affinity of the test antibody is maximal. To achieve this condition, the cells expressing the KB2F10 reference antibody as both competitor and test antibody were plated on several concentrations of isopropyl thiogalactoside (IPTG), an inducer of the lactose operon promoter. At 50 μM IPTG the cells plated quantitatively out to 75 μg/ml ampicillin, above which they declined rapidly. Since this is close to the midpoint of the dynamic range, it should be the condition of near-maximal sensitivity for selection of all reference antibody variants with affinities modestly above that of the reference antibody and higher. Thus, if the variant library were plated on an ampicillin concentration between 100 and 125 μg/ml ampicillin, the background PE due to reactivation by the KB2F10 reference antibody and unimproved variants will be between 0.4 and 0.01%, or 250-1000-fold lower than the PEs of variants with affinities less than 10-fold higher than that of the reference antibody. These background clones can then be eliminated by replating the selected clones 2-3 times under the same conditions, where with each replating the enrichment of higher-affinity variants over background is 250-1000-fold.

There are many ways to introduce random diversity into the coding sequence of an antibody without unduly compromising its original binding specificity or stability. These are described in detail in e.g., U.S. patent application Ser. No. 09/999,413, and include error-prone PCR, and various other PCR-based mutagenesis techniques such as DNA shuffling. In the Parsimonious Mutagenesis method (PM, Balint and Larrick, 1993, *Gene* 137:109-118) oligonucleotides encoding one or more CDRs are synthesized in which the codon for each position is doped with alternative nucleotides to allow pre-selected amino acid substitutions at pre-selected frequencies. The oligonucleotides are then used to prime amplification of the intervening V-region sequences, which are then ligated into the expression cassette in place of the reference V-region sequences. This creates an optimized library for affinity maturation in which each member has e.g., 1-2 coding changes per CDR, on average, and in which the diversity of coding changes at each position in the library is representative of the chemical diversity of natural amino acids. In this way, opportunities to pick up additional affinity without sacrificing the original affinity or stability are maximized. Most of the diversity of such libraries, covering e.g., all three CDRs in $V_H$ simultaneously, can be accessed in libraries of ~$10^9$ clones.

Thus, the first round of selection is performed by plating at least $10^9$ double transformants, expressing the CD40-BLIP-β-lactamase fusion, the KB2F10 Fab competitor, and the BIP-KB2F10 Fab fusion with PM library covering all three $V_H$ CDRs on 100 and 125 μg/ml ampicillin with 50M IPTG. Colonies appearing after overnight growth are pooled and the BIP-library member fusion plasmids purified and retransformed with the CD40-reporter/competitor plasmid. ~10 transformed cells per original colony are plated again on 100 and 125 μg/ml ampicillin with 50 μM IPTG. This process is repeated two more times to eliminate unimproved variants. At this point the remaining positives are plated on increasing concentrations of ampicillin to identify the highest affinity variants. Expression levels are also monitored, e.g., by immunoblot analysis, to identify any high-expression variants that may have been selected inspite of low affinity. The highest-affinity variants thus identified are then purified and characterized with respect to affinity and binding kinetics by e.g., surface plasmon resonance (Fägerstam et al. (1992) *J Chromatog* 597:397-410).

All publications, patents, and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An in vivo method of affinity maturation by auto-inhibited reactivation to obtain a binding molecule that has an enhanced affinity for a target antigen relative to a reference antibody that specifically binds to the target antigen, the method comprising:
   (a) recombinantly altering a population of host cells by
      (i) introducing into the host cells a nucleic acid encoding a competitor antibody that can be secreted and that binds to the target antigen with the same specificity as the reference antibody;
      (ii) introducing into the host cells a nucleic acid encoding a reactivator complex that can be secreted and that comprises a reactivator molecule covalently linked to the target antigen;
      (iii) introducing into the host cells a library of genes, each of which encodes an auto-inhibited responder complex that can be secreted and that comprises a responder molecule covalently linked to an inhibitor and to a candidate binding molecule that is an antibody, wherein the responder molecule is an enzyme and the inhibitor is an inhibitor of the enzyme;
   (b) incubating the host cells under conditions in which the competitor antibody, the reactivator complex, and the auto-inhibited responder library are expressed and secreted, where the responder molecule is activated when a candidate binding molecule competes for binding with the competitor antibody and binds to the target antigen; whereupon the reactivator displaces the inhibitor from the responder complex; and
   (c) detecting a signal from the responder molecule that corresponds to a candidate binding molecule affinity for the target antigen that is greater than that of the reference antibody, thereby identifying a candidate binding molecule with an enhanced affinity for the target antigen.

2. The method of claim 1, further wherein the competitor is the reference antibody.

3. The method of claim 2, further wherein the reference antibody is an Fab fragment.

4. The method of claim 2, further wherein the reference antibody is a single chain Fv (scFv).

5. The method of claim 1, further wherein the candidate binding molecules are single chain Fvs.

6. The method of claim 1, further wherein the candidate binding molecules are Fab fragments.

7. The method of claim 1, further wherein the candidate binding molecules are single V-region domains.

8. The method of claim 1, further wherein the candidate binding molecules are hybrid antibodies that have at least one CDR in a $V_H$ or $V_L$ that is different from the reference antibody and is from a natural antibody repertoire.

9. The method of claim 8, wherein the hybrid antibodies have either a $V_H$ or $V_L$ from the reference antibody and the corresponding $V_H$ or $V_L$ from a natural antibody repertoire.

10. The method of claim 1, further wherein the competitor is a nonhuman antibody and the candidate binding molecules comprise antibodies having at least one human variable region.

11. A method of affinity maturation by self-inhibited reactivation to obtain a binding molecule that has a higher affinity for a target antigen than that of a reference antibody that specifically binds to the target antigen, the method comprising:
   (a) recombinantly altering a population of host cells by
      (i) introducing into the host cells a nucleic acid encoding a competitor antibody that can be secreted and that binds to the target antigen with the same specificity as the reference antibody,
      (ii) introducing into the host cells a nucleic acid encoding an auto-inhibited responder complex that can be secreted and that comprises a responder molecule covalently linked to an inhibitor and to the target antigen, wherein the responder molecule is an enzyme and the inhibitor is an inhibitor of the enzyme,
      (iii) introducing into the host cells a library of genes, each encoding a reactivator complex that can be secreted, wherein each gene encodes a reactivator molecule covalently linked to a candidate binding molecule that is an antibody;
   (b) incubating the host cells under conditions in which the competitor antibody, the auto-inhibited responder complex, and the reactivator library complex are expressed and secreted, where the responder molecule is activated when a candidate binding molecule competes for binding with the competitor antibody and binds to the target antigen; whereupon the reactivator displaces the inhibitor from the responder complex; and
   (c) detecting a signal from the responder molecule that corresponds to a candidate binding molecule affinity for the target antigen that is greater than that of the reference antibody, thereby identifying a candidate binding molecule with an enhanced affinity for the target antigen.

12. The method of claim 11, further wherein the competitor is the reference antibody.

13. The method of claim 12, wherein the reference antibody is an Fab fragment.

14. The method of claim 12, wherein the reference antibody is a single chain Fv (scFv).

15. The method of claim 11, further wherein the candidate binding molecules are single chain Fvs.

16. The method of claim 11, wherein the candidate binding molecules are Fab fragments.

17. The method of claim 11, wherein the candidate binding molecules are single V-region domains.

18. The method of claim 11, further wherein the candidate binding molecules are hybrid antibodies that have at least one CDR in a $V_H$ or $V_L$ that is different from the reference antibody and is from a natural antibody repertoire.

19. The method of claim 18, wherein the hybrid antibodies have either a $V_H$ or $V_L$ from the reference antibody and the corresponding $V_H$ or $V_L$ from a natural antibody repertoire.

20. The method of claim 11, further wherein the reference antibody is a nonhuman antibody and the candidate binding molecules are antibodies having at least one human variable region.

21. The method of claim 1, wherein the host cells are prokaryotic.

22. The method of claim 21, wherein the host cells are *E. coli*.

23. The method of claim 1, wherein the host cells are yeast cells. or mammalian cells.

24. The method of claim 11, wherein the host cells are prokaryotic.

25. The method of claim 24, wherein the host cells are *E. coli*.

26. The method of claim 11, wherein the host cells are yeast cells or mammalian cells.

* * * * *